United States Patent [19]

Doehner, Jr.

[11] Patent Number: 4,843,162
[45] Date of Patent: Jun. 27, 1989

[54] ALKYL ESTERS OF SUBSTITUTED 2-METHYL-3-QUINOLINECARBOXYLIC ACID AND QUINOLINE-2,3-DICARBOXYLIC ACID

[75] Inventor: Robert F. Doehner, Jr., East Windsor, N.J.

[73] Assignee: American Cyanamid Company, Stamford, Conn.

[21] Appl. No.: 929,575

[22] Filed: Feb. 21, 1987

Related U.S. Application Data

[60] Division of Ser. No. 698,192, Feb. 4, 1985, Pat. No. 4,656,283, which is a continuation-in-part of Ser. No. 489,401, May 5, 1983, abandoned, which is a continuation-in-part of Ser. No. 381,815, May 25, 1982, abandoned.

[51] Int. Cl.$^4$ ............................................ C07D 215/48
[52] U.S. Cl. ...................................... 546/170; 560/44
[58] Field of Search ...................................... 546/17 Q

[56] References Cited

U.S. PATENT DOCUMENTS 4,459,408  7/1984  Maulding et al. .............. 546/170 X
4,459,409  7/1984  Ladner .............................. 546/170
4,675,432  6/1987  Maulding ........................ 546/170 X Primary Examiner—David B. Springer
Attorney, Agent, or Firm—Alice C. Brennan

[57] ABSTRACT

There are provided novel alkyl esters of substituted 2-methyl-3-quinolinecarboxylic acid and quinoline-2,3-dicarboxylic acid; novel dialkyl 3-(substituted)-phenylamino-2-ene-dioates, useful as intermediates for the preparation of highly effective 2-(2-imidazolin-2-yl)quinoline herbicidal agents and methods for the preparation thereof.

6 Claims, No Drawings

ALKYL ESTERS OF SUBSTITUTED 2-METHYL-3-QUINOLINECARBOXYLIC ACID AND QUINOLINE-2,3-DICARBOXYLIC ACID

This application is a division of application, Ser. No. 698,192, filed Feb. 4, 1985, now U.S. Pat. No. 4,656,283, which is a continuation-in-part of Ser. No. 489,401, filed May 5, 1983, abandoned, which is a continuation-in-part of Ser. No. 381,815, filed May 25, 1982, abandoned.

The invention relates to novel alkyl esters of substituted 2-methyl-3-quinolinecarboxylic acid and quinoline-2,3-dicarboxylic acid; dialkyl 3-(substituted)-phenylaminobut-2-ene-dioates, useful as intermediates in the preparation of 2-(2-imidazolin-2-yl)quinoline herbicides described in U.S. Pat. No. 4,638,068, and incorporated herein by reference thereto. The invention also relates to methods for the preparation of the above compounds.

More particularly, this invention relates to novel alkyl esters of substituted 2-methyl-3-quinolinecarboxylic acid and quinoline-2,3-dicarboxylic acid represented by formula (I) and dialkyl 3-(substituted)-phenylaminobut-2-ene-dioates of formula (VII) shown below.

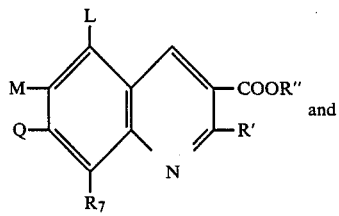

(I)

and

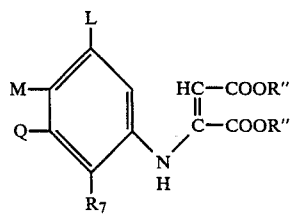

(VII)

wherein R' is $CH_3$ or COOR"; R" is $C_1$-$C_4$ alkyl; L, M, Q, and $R_7$ each represent members selected from the group consisting of H, halogen (Cl, Br, F or I), $C_1$-$C_4$ alkyl, $C_1$-$C_4$ alkoxy, $C_1$-$C_4$ alkylthio, $C_1$-$C_4$ alkylsulfonyl, halo($C_1$-$C_4$)alkyl, $NO_2$, CN, phenyl, phenoxy, difluoromethoxy, lowerlakylamino, chlorophenyl or phenoxy substituted with one Cl, $CF_3$, $NO_2$ or $CH_3$ group, with the proviso that at least one of L, M, Q, or $R_7$ is a substituent other than hydrogen and that only one of L, M, Q, or $R_7$ may represent a substituent other than hydrogen, halogen, $C_1$-$C_4$ alkyl or $C_1$-$C_4$ alkoxy. This invention also relates to methods for the preparation of compounds having the above structure, wherein R', R", L, M, Q, and $R^7$ are as described above; and, further, for compounds having the above structures wherein R' and R" are as described above, and L, M, Q, and $R_7$ are each hydrogen.

In accordance with the process of the present invention, an appropriately substituted aniline, depicted by formula (III),

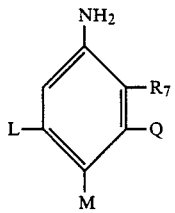

(III)

wherein L, M, Q, and $R_7$ each represent members selected from the group consisting of H, halogen (including F, Cl, Br, and I), $C_1$-$C_4$ alkyl, $C_1$-$C_4$ alkoxy, $C_1$-$C_4$ alkylthio, $C_1$-$C_4$ alkylsulfonyl, halo($C_1$-$C_4$)alkyl, $NO_2$, CN, phenyl, phenoxy, difluoromethoxy, loweralkylamino, chlorophenyl or phenoxy substituted with one Cl, $CF_3$, $NO_2$ or $CH_3$ group, with the proviso that only one of L, M, Q, or $R_7$ may represent a substituent other than hydrogen, halogen, $C_1$-$C_4$ alkyl or $C_1$-$C_4$ alkoxy is reacted with approximately an equimolar amount of a keto-ester depicted by formula ((IV) and having the structure:

$$R'—CO—CH_2—COOR" \qquad (IV)$$

wherein R' is $CH_3$ or COOR" and R" is $C_1$-$C_4$ alkyl. This reaction is optionally conducted in the presence of an organic sulfonic acid such as p-toluenesulfonic acid hydrate, camphorsulfonic acid, or aniline hydrochloride, in the presence of an organic solvent such as cyclohexane, toluene, benzene, xylene, monochlorobenzene, orthodichlorobenzene and mixtures thereof, or the like at a temperature from about 20° to 110° C. It is preferred to continuously remove the water which is formed during the reaction by distillation either at atmospheric or under reduced pressures of as low as 50 mm of Hg while maintaining the reaction temperature in a range of 75° to 80° C. The reaction yields the β-anilino-α,β-unsaturated ester of formula (II), i.e.,

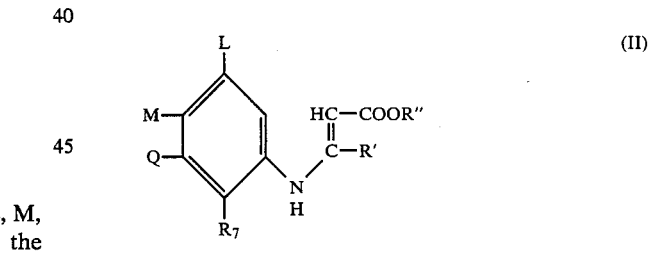

(II)

wherein L, M, Q, $R_7$, R', and R" are as described above.

The thus-formed β-anilino-α,β-unsaturated ester of formula (II) is then reacted with an approximately equimolar amount of an immonium salt having the structure:

(V)

wherein R'" is $C_1$-$C_4$ alkyl or

(Va)

wherein n is 4 or 5, and referred to respectively as formula (V) or (Va). The reaction is conducted in the presence of a hydrocarbon solvent such as toluene or a chlorinated hydrocarbon solvent such as methylene chloride, dichloroethane, orthodichlorobenzene, chlorobenzene, or mixtures thereof, at a temperature between about 40° and 110° C., for a period of time sufficient to essentially complete the reaction and yield the formula (I) alkyl ester of 2-methyl-3-quinolinecarboxylic acid, if R' is CH₃ in the formula (II) β-anilino-α,β-unsaturated ester; or the quinoline-2,3-dicarboxylate if R' is COOR" in the formula (II) β-anilino-α,β-unsaturated ester.

Alternatively, the formula (III) substituted aniline, wherein L, M, Q, and R₇ are as described above, can be reacted with about an equimolar amount of a formula (VI) acetylene dicarboxylate having the structure:

R"OOC—C≡C—COOR", where R" is C₁-C₄ alkyl. This reaction is generally carried out in the presence of a solvent such as dichloroethane or a C₁-C₄ alcohol such as methanol, at a temperature between 0° and 100° C. to yield a β-anilino-α,β-unsaturated ester as formula (VII). The β-anilino-α,β-unsaturated ester of formula (VII is then reacted with an immonium salt depicted by formula (V) having the structure:

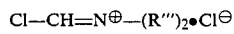

Cl—CH=N⊕—(R''')₂•Cl⊖ where R''' is C₁-C₆ alkyl or (Va) having the structure:

Cl—CH=N⊕ ⟨(CH₂)ₙ⟩·Cl⊖ where n is 4 or 5. While the anion in formulas (V) and (Va) is shown as Cl⊖, it should be recognized that when POCl₃ is used to prepare the Vilsmeier reagent, the anion is PO₂CL₂⊖. This reaction is generally conducted in the presence of a solvent such as methylene chloride, dichloroethane, monochlorobenzene, orthodichlorobenzene, or toluene at a temperature between 40° and 110° C. for a period of time sufficient to complete the reaction and yield the quinoline-2,3-dicarboxylate shown as formula (Ia) having the structure:

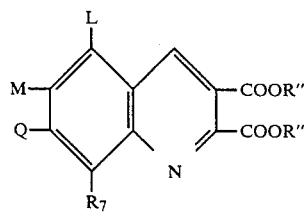

(Ia)

wherein L, M, Q, R₇ and R" are as described above.

The immonium salt formula (V) or (Va) utilized in the above cyclization reactions may, hereafter, be referred to as the Vilsmeier reagent. This reagent may be generated from a (alkyl or phenyl) formamide reaction with POCl₃, COCl₂, ClCO—COCl or SOCl₂ in a hydrocarbon or chlorinated hydrocarbon solvent.

Conversion of the formula (I) alkyl ester of 2-methyl-3-quinolinecarboxylic acid, to the 2,3-quinolinedicarboxylic acid of formula (VIII) is achieved by a very distinctive process involving the simultaneous oxidation of the R' methyl function and the hydrolysis of the ester function R" of the alkyl ester of 2-methyl-3-quinolinecarboxylic acid. This is accomplished by admixing the formula (I) alkyl ester of 2-methyl-3-quinolinecarboxylic acid with a sufficient amount of water to give a 0.02 to 1.0M solution of said compound and adding thereto about 5–15% by weight of aqueous alkali metal hydroxide such as sodium or potassium hydroxide. The mixture is stirred to provide an essentially homogenous mixture. In practice, it has been found beneficial, although not essential, for the formula (I) starting material to have some solubility in the reaction medium, either initially or after saponification of the functional group R". The reaction mixture is then treated with from 3.0 to 4.0 molar equivalents (preferably up to 1 molar equivalent excess) of nickel peroxide. Addition of the nickel peroxide to the mixture can be made in small increments or all at once. However, the temperature of the reaction mixture should be maintained at from 0° to 30° C., and the mixture should be stirred until the oxidation and hydrolysis are essentially complete. At the end of the reaction time, no starting material is detectable, and the insoluble inorganic materials are removed by decantation, filtration, or the like. The filtrate is then acidified to pH 2 with hydrochloric acid to give the formula (VIII) to quinoline-2,3-dicarboxylic acid wherein L, M, Q, R₇, are as described above and has the structure:

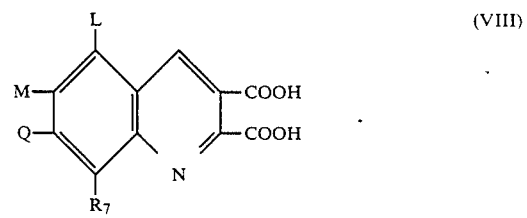

(VIII)

This process is graphically illustrated in Flow Diagram I and described in U.S. Pat. No. 4,459,409 and incorporated herein by reference thereto.

Following isolation, the formula (VIII) quinoline-2,3-dicarboxylic acid is heated to about 70° to 95° C. with an excess of acetic anhydride to yield the formula (IV) 2,3-quinolinedicarboxylic acid anhydride, having the structure:

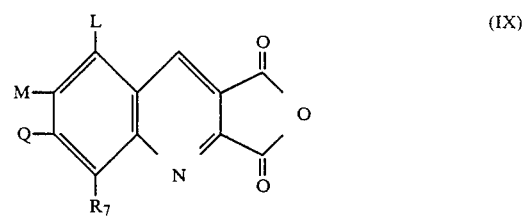

(IX)

wherein L, M, Q and R₇ are as described above. A cosolvent such as pyridine or pyridine-dimethoxyethane may also be used in this reaction, but is not essential to obtain the desired product.

Reaction of the formula (IX) 2,3-quinolinedicarboxylic acid anhydride with a formula (X) aminocarboxamide or aminothiocarboxamide having the structure:

$$NH_2-\underset{R_2}{\underset{|}{\overset{R_1}{\overset{|}{C}}}}-CW-NH_2 \quad (X)$$

wherein R₁ is C₁-C₄ alkyl; R₂ is C₁-C₄ alkyl or C₃-C₆ cycloalkyl; and when R₁ and R₂ are taken together they may represent $C_3$-$C_6$ cycloalkyl optionally substituted with methyl; and W is sulfur or oxygen; is preferably carried out using equivalent amounts of the anhydride and carboxamide or thiocarboxamide in the presence of an inert organic solvent such as tetrahydrofuran, diethyl ether, or the like at a temperature between 0° to 30° C. When the reaction is essentially complete, the solvent is evaporated, and the residue triturated with a solvent such as ethyl acetate to afford an isomeric mixture of the 3-quinolinecarboxylic acid and the quinaldic acid shown, respectively, as formula (XIa) having the structure:

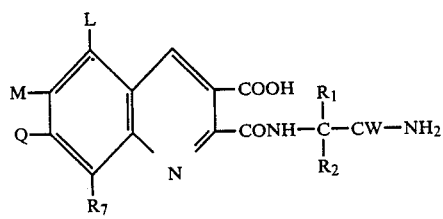

(XIa)

wherein L, M, Q, $R_7$, $R_1$, $R_2$ and W are as described above, and formula (XIb) having the structure:

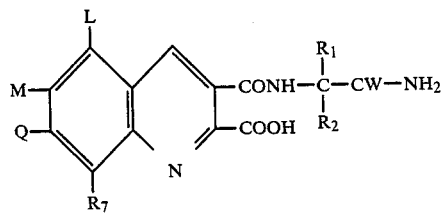

(XIb)

where L, M, Q, $R_7$, $R_1$, $R_2$ and W, are as described above.

The thus-formed mixture is then heated to a temperature of from 25° to about 110° C. with about 2 to 20 molar equivalents of aqueous or aqueous alcoholic sodium or potassium hydroxide, preferably under a blanket of inert gas such as nitrogen. The mixture is cooled to about 25° C. and acidified to pH 2 to 4, with a strong mineral acid such as hydrochloric acid or sulfuric acid to give the herbicidally effective 2-(5,5-disubstituted-4-oxo(or thiono)-2-imidazolin-2-yl)-3-quinolinecarboxylic acids, encompassed by formula (XII); wherein $R_1$ is $C_1$-$C_4$ alkyl; $R_2$ is $C_1$-$C_4$ alkyl or $C_3$-$C_6$ cycloalkyl; and when $R_1$ and $R_2$ are taken together, they may represent $C_3$-$C_6$ cycloalkyl optionally substituted with methyl, and when $R_1$ and $R_2$ are not the same, the optical isomers thereof; W is 0 or S; and L, M, Q, and $R_7$ each represent members selected from the group consisting of hydrogen, halogen, $C_1$-$C_4$ haloalkyl, difluoromethoxy, diloweralkylamino, $C_1$-$C_4$ alkoxy or halogen; with the proviso that only one of L, M, Q, or $R_7$ may represent a substituent other than hydrogen, halogen, $C_1$-$C_4$ alkyl or $C_1$-$C_4$ alkoxy. The above reactions are graphically illustrated in Flow Diagram I below.

The base cyclization is disclosed in U.S. Pat. No. 4,518,780 and incorporated herein by reference thereto.

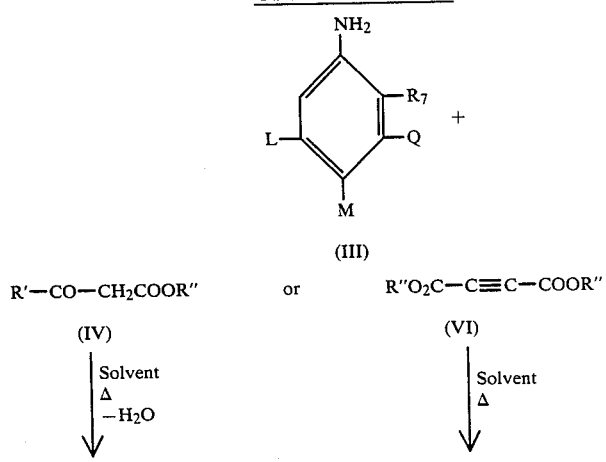

-continued
FLOW DIAGRAM I
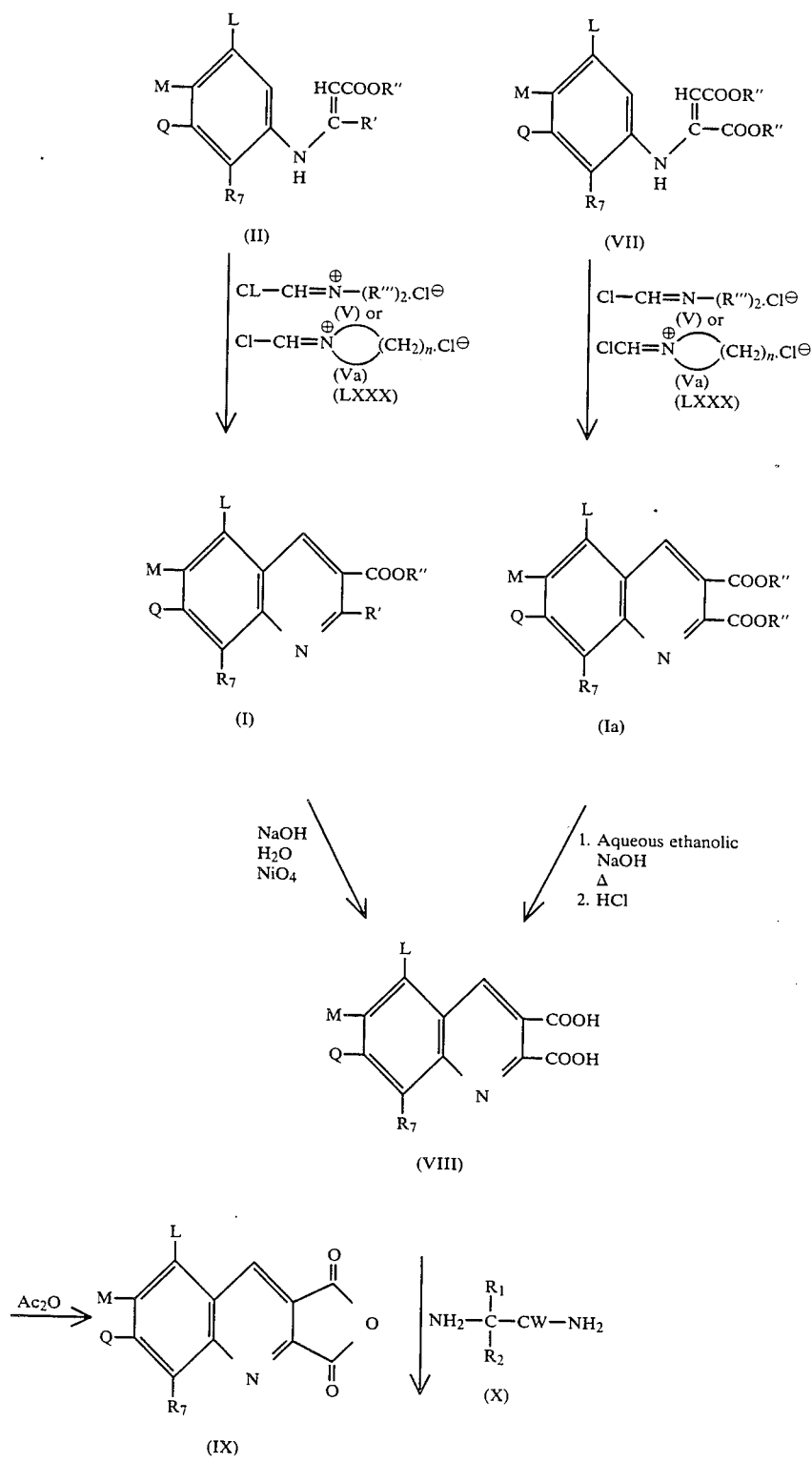

-continued
FLOW DIAGRAM I

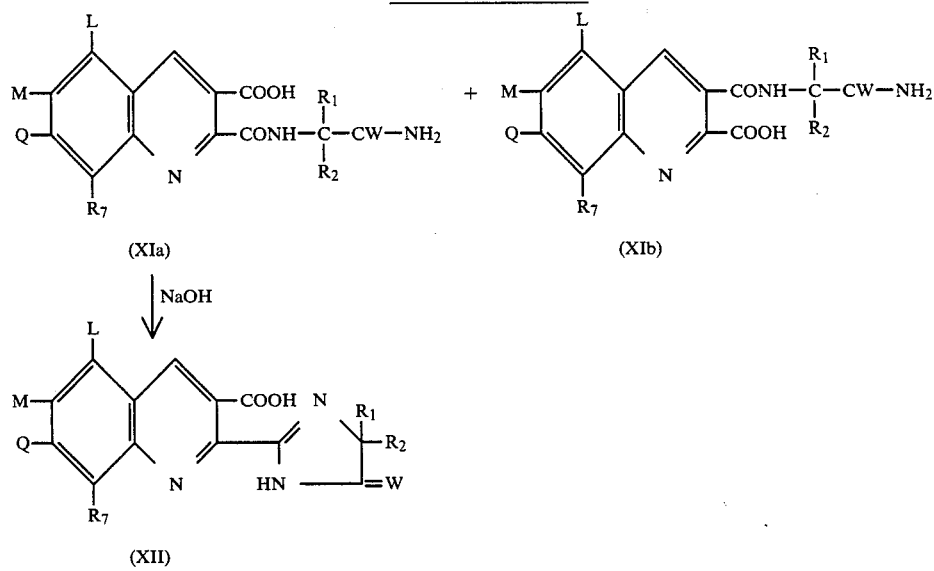

(XIa)    (XIb)

↓ NaOH (XII)

The formula (XII) 2-(5,5-disubstituted-4-oxo(or thiono)-2-imidazolin-2-yl)-3-quinolinecarboxylic acids are highly effective herbicidal agents useful for controlling a variety of annual and perennial monocotyledonous and dicotyledonous plants. These compounds are herbicidally effective for controlling weeds indigenous to both dry land and wet land areas. They are also useful as aquatic herbicides and are unique in their effectiveness in controlling the above-said plants when applied to the foliage thereof or to soil or water containing seeds or other propagating organs of said plants such as tubers, rhizomes or stolons, at rates of from about 0.025 to 8.0 kg/ha, and preferably at rates from about 0.032 to 2.0 kg/ha.

For application to undesirable plants, these compounds can be formulated as wettable powders, emulsifiable concentrates, flowable liquids granular formulations and the like, and applied as aqueous sprays or granular solids to the foliage of the plants or to soil or water containing seeds or other propagating organs thereof.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5 to 25% by weight of the active ingredient in about 65 to 95% by weight of N-methyl-pyrrolidone, isophorone, butyl cellosolve, methylacetate or the like and dispersing therein about 5 to 10% by weight of nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of Diethyl 3-phenylaminobut-2-ene-dioate

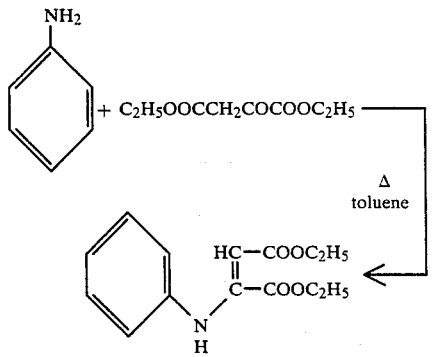

Aniline (0.217 mol) and diethyloxalacetate (0.217 mol) are mixed in toluene (500 mL) and heated at reflux, i.e., about 110° C., under a water separator for approximately one hour. The toluene is then removed under vacuum to afford the desired product, i.e., diethyl 3-phenylaminobut-2-ene-dioate.

Following the above procedure, but utilizing a substituted aniline for aniline and/or dimethyloxalacetate for diethyloxalacetate, yields the substituted-phenylaminobut-2-ene-dioates illustrated below.

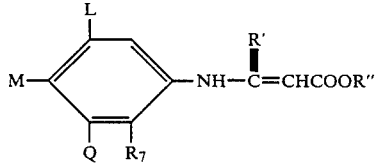

| L | M | Q | R7 | R' | R'' | mp °C. |
|---|---|---|---|---|---|---|
| H | NO2 | H | H | CO2CH3 | CH3 | 119.5–120.5 |
| H | H | H | OCH3 | CO2CH3 | CH3 | 71.0–73 |
| H | CN | H | H | CO2CH3 | CH3 | 107.0–109 |
| H | SCH3 | H | H | CO2CH3 | CH3 | 50.0–54 |
| H | C6H5 | H | H | CO2CH3 | CH3 | 60.0–63 |
| H | CF3 | H | H | CO2CH3 | CH3 | oil |
| H | H | CH3 | CH3 | CO2CH3 | CH3 | 127.0–129.5 |
| H | OCH3 | H | H | CO2CH3 | CH3 | — |
| H | CH3 | CH3 | H | CO2CH3 | CH3 | — |
| OCH3 | H | H | OCH3 | CO2C2H5 | C2H5 | oil |
| H | C2H5 | H | H | CO2CH3 | CH3 | oil |
| H | Br | H | H | CO2CH3 | CH3 | 83.0–86 |
| H | H | OC2H5 | H | CO2CH3 | CH3 | oil |
| H | C4H9 | H | H | CO2CH3 | CH3 | oil |
| H | OCHF2 | H | H | CO2CH3 | CH3 | oil |
| Cl | H | H | OCH3 | CO2CH3 | CH3 | not isolated |
| H | H | F | H | CO2CH3 | CH3 | 112–115 |
| H | H | H | H | CO2C2H5 | C2H5 | oil |
| H | OCH3 | OCH3 | H | CO2C2H5 | C2H5 | not isolated |

EXAMPLE 2

Preparation of Ethyl-3-phenylaminobut-2-enoate

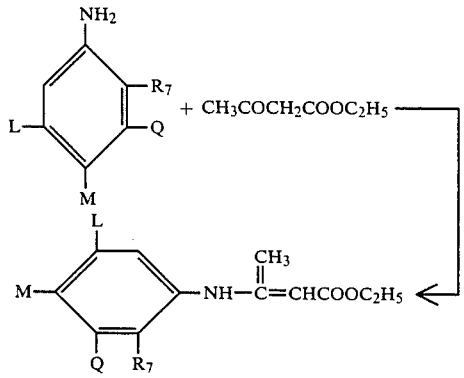

Aniline (0.20 mol) and ethylacetoacetate (0.20 mol) are mixed in toluene (200 mL) containing 0.04 g of p-toluenesulfonic acid-hydrate and heated at reflux under a water separator for one hour. The toluene is removed under vacuum to afford the ethyl-3-phenylaminobut-2-enoate which can be used as is for the preparation of the ethyl 2-methyl-3-quinolinecarboxylate.

| L | M | Q | R7 | m.p. °C. |
|---|---|---|---|---|
| OCH3 | H | H | OCH3 | Not isolated |

EXAMPLE 3

Preparation of Dimethyl 3-phenylaminobut-2-ene-dioate

To a stirred solution of dimethylacetylenedicarboxylate (DMAD, 0.10 mol) in 50 mL of ethylene dichloride (EDC), is slowly added a solution of aniline (0.10 mol) in 15 mL of EDC. The temperature of the reaction mixtures is maintained below 30° C. and stirring is continued for about one hour until the reaction is essentially complete. The EDC is then removed under vacuum to afford the dimethyl 3-phenylaminobut-2-ene-dioate.

Following the above procedure but utilizing a substituted aniline for aniline, yields the ring substituted dimethyl 3-phenylaminobut-2-ene-dioates illustrated below:

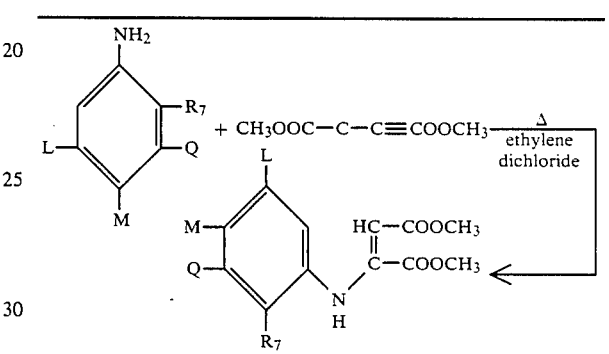

| L | M | Q | R7 | m.p. °C. |
|---|---|---|---|---|
| H | Cl | H | H | Not isolated |
| H | OC6H5 | H | H | Not isolated |
| H | H | F | H | 112–115 (.2 mm) |
| H | H | H | F | 62–65 |
| H | F | Cl | H | 160–161 (.9 mm) |
| H | OCF3 | H | H | 48–51 |
| F | H | H | OCH3 | 76–81 |
| H | CH3 | H | CH3 | 114–116 |
| H | OCH2C6H5 | H | H | 105–108 |
| H | SC6H5 | H | H | 76–80 |
| H | H | C6H5 | H | Not isolated |
| H | CH2C6H5 | H | H | Not isolated |
| H | COC6H5 | H | H | 97–100 |
| H | N(CH3)C6H5 | H | H | Not isolated |
| OCH3 | H | OCH3 | H | 56–59 |
| F | H | H | OCH3 | 76–81 |

EXAMPLE 4

Preparation of Dimethyl 2,3-quinolinedicarboxylate wherein the Vilsmeier reagent is prepared in situ To a solution of dimethylformamide (DMF, 0.10 mol) in ethylene chloride (EDC, 100 mL), cooled in an ice bath, is added dropwise with stirring phosphorous oxychloride (POCl3, 0.10 mol). The resulting solution is stirred for one and one-half hours at room temperature and then cooled in an ice bath. To the cooled solution is then added, in small increments, a solution of dimethyl 3-phenylaminobut-2-ene-dioate (0.10 mol) in ethylene dichloride. The resulting mixture is thereafter heated to reflux for three hours, cooled, and washed with half saturated brine. The organic phase is washed with half saturated brine. The organic phase is separated from the aqueous phase and dried. The solvent is removed under vacuum, and the residue recrystallized from methanol to afford 18.2 g (0.074 mol) of dimethyl-2,3-quinolinedicarboxylate, mp 105°–106.5° C.

Using the above procedure and the appropriate 3-phenylaminobut-2-ene-dioate yields the dialkyl 2,3-quinolinedicarboxylate or 2-methyl-3-quinolinecarboxylates reported below are obtained.

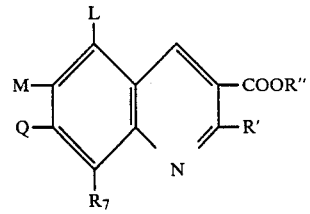

| L | M | Q | $R_7$ | R' | R'' | mp °C. |
|---|---|---|---|---|---|---|
| H | H | H | H | $CH_3$ | $C_2H_5$ | 65.0–69 |
| H | H | H | H | $CO_2C_2H_5$ | $C_2H_5$ | 53.0–54.5 |
| H | $NO_2$ | H | H | $CO_2CH_3$ | $CH_3$ | 174.0–174.5 |
| H | H | H | $OCH_3$ | $CO_2CH_3$ | $CH_3$ | 95.0–96 |
| H | CN | H | H | $CO_2CH_3$ | $CH_3$ | 185.5–187.5 |
| H | $SCH_3$ | H | H | $CO_2CH_3$ | $CH_3$ | 136.0–138 |
| H | $C_6H_5$ | H | H | $CO_2CH_3$ | $CH_3$ | >300 |
| H | $CF_3$ | H | H | $CO_2CH_3$ | $CH_3$ | 123.5–125 |
| H | H | $CH_3$ | $CH_3$ | $CO_2CH_3$ | $CH_3$ | 150.5–152 |
| H | $OCH_3$ | H | H | $CO_2CH_3$ | $CH_3$ | 129.0–131 |
| H | $CH_3$ | $CH_3$ | H | $CO_2CH_3$ | $CH_3$ | 116.0–118 |
| $OCH_3$ | H | H | $OCH_3$ | $CO_2C_2H_5$ | $C_2H_5$ | 82.0–85 |
| H | $OC_6H_5$ | H | H | $CO_2CH_3$ | $CH_3$ | 138.0–140 |
| H | $C_2H_5$ | H | H | $CO_2CH_3$ | $CH_3$ | 60.0–61.5 |
| H | $C_4H_9$ | H | H | $CO_2CH_3$ | $CH_3$ | oil |
| H | Br | H | H | $CO_2CH_3$ | $CH_3$ | 157.0–158 |
| H | H | $OC_2H_5$ | H | $CO_2CH_3$ | $CH_3$ | — |
| H | $OCHF_2$ | H | H | $CO_2CH_3$ | $CH_3$ | 84.0–85 |
| H | Cl | H | H | $CO_2CH_3$ | $CH_3$ | 153.0–155 |
| Cl | H | H | H | $OCH_3$ | $CO_2CH_3$ | $CH_3$ | 120.0–122 |
| $OCH_3$ | H | H | Cl | $CO_2CH_3$ | $CH_3$ | 174.0–176 |
| H | H | H | F | $CO_2CH_3$ | $CH_3$ | 114.0–116 |
| H | $OCH_3$ | $OCH_3$ | H | $CO_2C_2H_5$ | $C_2H_5$ | 129.5–131 |
| $OCH_3$ | H | H | $OCH_3$ | $CH_3$ | $C_2H_5$ | 133–134 |
| H | F | Cl | H | $COCH_3$ | $CH_3$ | 135–136 |
| F | H | H | H | $OCH_3$ | $CO_2CH_3$ | $CH_3$ | 153–156 |
| H | H | H | F | $CO_2CH_3$ | $CH_3$ | 105–107 |

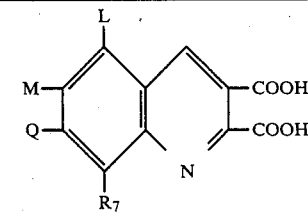

| L | M | Q | $R_7$ | R' | R'' | mp °C. |
|---|---|---|---|---|---|---|
| H | $OCF_3$ | H | H | $CO_2CH_3$ | $CH_3$ | 86–89 |
| H | $CH_3$ | H | $CH_3$ | $CO_2CH_3$ | $CH_3$ | 123.5–125.5 |
| H | $OCH_2C_6H_5$ | H | H | $CO_2CH_3$ | $CH_3$ | 69–72 |
| H | $SC_6H_5$ | H | H | $CO_2CH_3$ | $CH_3$ | 95–100 |
| H | H | $C_6H_5$ | H | $CO_2CH_3$ | $CH_3$ | 123–126 |
| H | $CH_2C_6H_5$ | H | H | $CO_2CH_3$ | $CH_3$ | 98–101 |
| H | $COC_6H_5$ | H | H | $CO_2CH_3$ | $CH_3$ | 129–132 |
| H | $N(CH_3)C_6H_5$ | H | H | $CO_2CH_3$ | $CH_3$ | 100–103 |
| $OCH_3$ | H | $OCH_3$ | H | $CO_2CH_3$ | $CH_3$ | 191–194 |
| F | H | H | $OCH_3$ | $CO_2CH_3$ | $CH_3$ | 153–156 |

EXAMPLE 5

Preparation of 2,3-quinolinedicarboxylic acid

To a solution of diethyl 2,3-quinolinedicarboxylate (0.162 mol) in ethanol (150 mL) is added a solution of sodium hydroxide (0.50 mol) in water (400 mL). The mixture is heated at reflux for five hours, and the ethanol then removed by distillation at atmospheric pressure. The solution is cooled in an ice bath, diluted with water (100 mL), and acidified with concentrated hydrochloric acid, added in small increments. The precipitate is filtered, washed with water, and air dried to afford the desired 2,3-quinolinedicarboxylic acid as the trihydrate; mp 271°–277° C.

Utilizing the above procedure, but substituting the appropriate substituted or unsubstituted dialkyl 2,3-quinolinedicarboxylate, yields the substituted or unsubstituted 2,3-quinolinedicarboxylic acids reported below.

| L | M | Q | $R_7$ | mp °C. |
|---|---|---|---|---|
| H | $NO_2$ | H | H | 295.0–297 (dec) |
| H | H | H | $OCH_3$ | 270.0–275 |
| H | $CF_3$ | H | H | >300 |
| H | $C_6H_5$ | H | H | >300 |
| H | $SCH_3$ | H | H | >305 |
| H | H | $CH_3$ | $CH_3$ | 148.0–150 |
| H | $OCH_3$ | H | H | — |
| $OCH_3$ | H | H | $OCH_3$ | 274.0–276 |
| H | $C_2H_5$ | H | H | 190.0–195 |
| H | $C_4H_9$—n | H | H | — |
| H | $OC_6H_5$ | H | H | — |
| H | $OCHF_2$ | H | H | 226.0 |
| H | H | $OC_2H_5$ | H | 197.0–198 (dec) |
| H | Br | H | H | 254.0–255 |
| H | Cl | H | H | 251.0–253 |
| Cl | H | H | $OCH_3$ | 310.0–320 |
| $OCH_3$ | H | H | Cl | 275.0–285 |
| H | $OCH_3$ | $OCH_3$ | H | 262.0–263 |
| H | H | F | H | 290.0–292 |

-continued

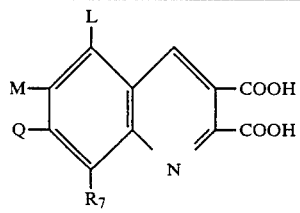

| L | M | Q | R7 | mp °C. |
|---|---|---|----|--------|
| H | CN | H | H | >300 |
| H | F | Cl | H | 288.0–291 |
| H | H | H | F | 246.0–249 |

EXAMPLE 6

Preparation of 2,3-quinolinedicarboxylic acid

Three grams of 2-methylquinoline-3-carboxylic acid (0.012 mol of 3.5 hydrate) is dissolved in 100 mL 15% sodium hydroxide solution and an additional 100 mL $H_2O$ is added. The mixture became homogenous. At room temperature is added all at once, 12.0 g nickel peroxide, (0.044 mol, 3.q eq. 20% excess) and the mixture is stirred magnetically for 12 hours. The insolubles are removed by vacuum filtration and washed with water. The filtrate is acidified to pH of 2 and a solid fluffy precipitate forms. It is filtered and dried to give 2.48 g of quinoline-2,3-dicarboxylic acid which is hydrated with 1.3 mol $H_2O$/mol compound as determined by NMR. More product is isolated from the aqueous filtrate by concentration and filtration, bringing the total actual yield to 2.88 g or 100%. The IR Spectrum is identical to product obtained in Example 5 above and has a mp of 271°–277° C.

EXAMPLE 7

Preparation of 2,3-quinolinedicarboxylic anhydride

A mixture of 2,3-quinolinedicarboxylic acid-trihydrate (0.141 mol) in acetic anhydride (125 mL) is heated at 85° C. for one-half hour and then at 100° C. for one hour. The reaction mixture is then cooled to room temperatures, filtered and the solids washed with ethyl ether to afford the desired 2,3-quinolinedicarboxylic anhydride, mp 255°–228° C.

Utilizing the above procedure but substituting the appropriately substituted 2,3-quinolinedicarboxylic acid for 2,3-quinolinedicarboxylic acid-trihydrate, yields the following substituted 2,3-quinolinedicarboxylic anhydrides.

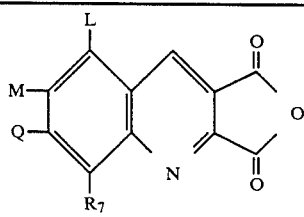

| L | M | Q | R7 | mp °C. |
|---|---|---|----|--------|
| H | OC6H5 | H | H | 187.0–188 |
| H | NO2 | H | H | 225.0–228 (dec) |
| H | C6H5 | H | H | 258.5–261 |
| H | H | CH3 | CH3 | 270.0–272 |
| H | OCH3 | H | H | 208.0–210 |

-continued

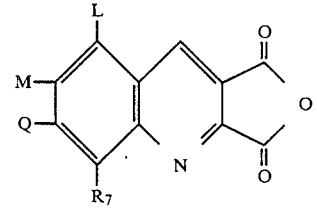

| L | M | Q | R7 | mp °C. |
|---|---|---|----|--------|
| H | CH3 | CH3 | H | — |
| H | SCH3 | H | H | 247.0–251 |
| H | CN | H | H | 190.0–192 |
| H | H | H | OCH3 | — |
| H | C2H5 | H | H | 212.0–214 |
| H | C4H9—n | H | H | ~160.0–210 |
| OCH3 | H | H | H | 266.0–267 |
| H | CF3 | H | H | 157.0–159 |
| H | OCHF2 | H | H | 157.5–158.5 |
| H | Cl | H | H | 243.0–245 |
| H | H | OC2H5 | H | 222.0–224 |
| Cl | H | H | OCH3 | 240.0–242 |
| OCH3 | H | H | Cl | 228.0–236 |
| H | OCH3 | OCH3 | H | 257.0–258 |
| H | H | F | H | not pure |
| H | F | Cl | H | 223.0–226 |

EXAMPLE 8

Preparation of 2-[(1-carbamoyl-1,2-dimethylpropyl)carbamoyl]-3-quinolinecarboxylic acid A solution of 2,3-quinolinedicarboxylic anhydride (0.037 mol) in tetrahydrofuran (THF, 250 mL) is stirred at 5° C. under a drying tube, and a solution of 2-amino-2,3-dimethylbutyramide (0.037 mol) in THF (50 mL) added thereto, in small increments, over a 15 minute period. The reaction mixture is allowed to warm slowly to room temperature for an extended period of time, i.e. about 17 hours. The solvent is evaporated in vacuo to afford a gummy residue, which is triturated with hot ethyl acetate (400 mL) and then filtered to afford the desired 2-[(1-carbamoyl-1,2-dimethylpropyl)carbamoyl]-3-quinolinecarboxylic acid, mp 172.5°–173.5° C.

Utilizing the above procedure but substituting the appropriately substituted 2,3-quinolinedicarboxylic anhydride for 2,3-quinolinedicarboxylic anhydride yields the following 2-[(1-carbamoyl-1,2-dimethylpropyl)-carbamoyl]-3-quinolinecarboxylic acids.

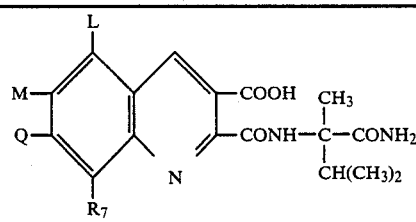

| L | M | Q | R₇ | mp °C. |
|---|---|---|---|---|
| H | OC₆H₅ | H | H | 189.0-190 |
| H | NO₂ | H | H | 225.0-227 (dec) |
| H | H | H | OCH₃ | foam |
| H | CF₃ | H | H | 222.0-224 |
| H | CN | H | H | — |
| H | SCH₃ | H | H | 186.0-188 |
| H | C₆H₅ | H | H | 189.5-192 |
| H | H | CH₃ | CH₃ | 246.0-250 |
| H | OCH₃ | H | H | — |
| H | CH₃ | CH₃ | H | — |
| H | C₂H₅ | H | H | 198.0-199 |
| H | C₄H₉ | H | H | 163.0-164 |
| OCH₃ | H | H | OCH₃ | 209.0-209.5 |
| H | CF₃ | H | H | 222.0-224 |
| H | OCHF₂ | H | H | 194.0-196 |
| H | Br | H | H | 234.0-235 |
| H | Cl | H | H | 225.0-226 (dec) |
| H | H | OC₂H₅ | H | 194.5-195.5 |
| H | H | F | H | 174.0-176 |

EXAMPLE 9

Preparation of 2-(5-isopropyl-5-methyl-4-oxo-2-imidazolin-2-yl)-3-quinolinecarboxylic acid A solution of 2-[(1-carbamoyl-1,2-dimethylpropyl)-carbamoyl]-3-quinolinecarboxylic acid (0.152 mol), in water (50 mL) containing sodium hydroxide (0.06 mol) is heated at 75° to 80° C. for two hours. The solution is cooled in an ice bath and acidified with concentrated hydrochloric acid, added in small increments. The resulting precipitate is filtered, washed with water, air dried, and recrystallized from acetone to afford the 2-(5-isopropyl-5-methyl-4-oxo-2-imidazolin-2-yl)-3-quinolinecarboxylic acid, mp 239°-243.5° C.

Utilizing the above procedure and substituting the appropriately substituted 3-quinolinecarboxylic acid for 2-[(1-carbamoyl-1,2-dimethylpropyl)carbamoyl]-3-quinolinecarboxylic acid yields the compounds illustrated below.

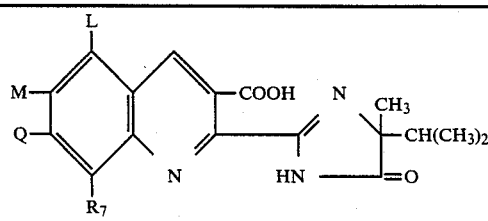

| | L | M | Q | R₇ | mp °C. |
|---|---|---|---|---|---|
| | H | NO₂ | H | H | 241.5-242 |
| | H | OC₆H₅ | H | H | 223.0 |
| | H | H | H | OCH₃ | 258.0-261 |
| | H | CF₃ | H | H | 215.0-218 |
| | H | C₆H₅ | H | H | 290.5-212 |
| | H | CH₃ | CH₃ | H | 238.0-240 |
| | OCH₃ | H | H | OCH₃ | 249.0-250 |
| | H | SCH₃ | H | H | 264.0-265 |
| | H | C₂H₅ | H | H | 179.5-180.5 |
| | H | C₄H₉ | H | H | 149.0-150.5 |
| | H | H | CH₃ | CH₃ | 238.0-240 |
| | H | OCHF₂ | H | H | 208.0-209 |
| (+) | H | Cl | H | H | 235.0-237 |
| | H | Cl | H | H | 220.0-223 |

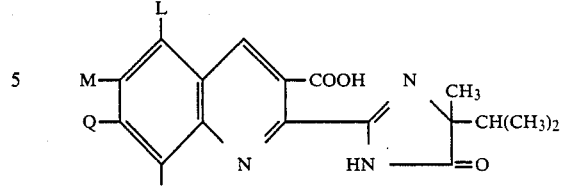

| L | M | Q | R₇ | mp °C. |
|---|---|---|---|---|
| Cl | H | H | OCH₃ | 220.0-222 |
| OCH₃ | H | H | Cl | 224.5-228 |
| H | H | F | H | 219.0-221 |
| H | OCH₃ | OCH₃ | H | 242.0-245 |
| H | H | OC₂H₅ | H | 237.5-239 |
| H | F | Cl | H | 259-262 |
| H | H | H | F | 269-272 |
| H | OCF₃ | H | H | 207-210 |
| H | OCH₂C₆H₅ | H | H | 189-191 |
| H | SC₆H₅ | H | H | 243-245 |
| H | H | C₆H₅ | H | 257-261 |
| H | CH₂C₆H₅ | H | H | 206-210 |
| H | COC₆H₅ | H | H | 263-267 |
| H | N(CH₃)C₆H₅ | H | H | 193-197 |
| OCH₃ | H | OCH₃ | H | 243-247 |

EXAMPLE 10

Postemergence herbicidal evaluation of test compounds

The postemergence herbicidal activity of the compounds of the present invention is demonstrated by the following tests, wherein a variety of monocotyledonous and dicotyldonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.25 kg of 10 kg per hectare of activity compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided below. The data obtained are recorded in Table I below.

| Rating System | % Difference in growth from the Check* |
|---|---|
| 0 - No effect | 0 |
| 1 - Possible effect | 1-10 |
| 2 - Slight effect | 11-25 |
| 3 - Moderate effect | 26-40 |
| 5 - Definite injury | 41-60 |
| 6 - Herbicidal effect | 61-75 |
| 7 - Good herbicidal effect | 76-90 |
| 8 - Approaching complete kill | 91-99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green Foxtail | (Setaria viridis) |
| Purple Nutsedge | (Cyperus rotundus L.) |
| Wild Oats | (Avena fatua) |
| Quackgrass | (Agropyron repens) |
| Field Bindweed | (Convolvulus arvensis L.) |
| Morningglory | (Ipomoea purpurea) |
| Ragweed | (Ambrosia artemisiifolia) |
| Velvetleaf | (Abutilon theophrasti) |
| Barley | (Hordeum vulgare) |
| Corn | (Zea mays) |
| Rice | (Oryza sativa) |
| Soybean | (Glycine max) |
| Sunflower | (Helianthus annus) |
| Wheat | (Triticum aestivum) |

TABLE I

POST-EMERGENCE TESTS - RATES IN KG/HA

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE, NATO | SOY-BEAN WI | SUN-FLR XXX | S WHEAT ER |
|---|---|---|---|---|---|---|---|---|---|---|---|---|---|---|---|---|
| 2-(5-Isopropyl-5-methyl-4-oxo-2-imidazolin-2-yl)-3-quinolinecarboxylic acid | 8.000 | 9.0 | 9.0 | 9.0 | 9.0 | 9.0 | 9.0 | 9.0 | | 9.0 | | 9.0 | 9.0 | 0.5 | 9.0 | 9.0 |
| | 4.000 | 9.0 | 9.0 | 8.5 | 9.0 | 9.0 | 9.0 | 8.5 | 9.0 | 9.0 | | 9.0 | 9.0 | 0.0 | 9.0 | 9.0 |
| | 2.000 | 9.0 | 9.0 | 8.3 | 9.0 | 8.9 | 8.7 | 8.3 | 8.8 | 8.6 | | 9.0 | 8.7 | 0.1 | 9.0 | 8.9 |
| | 1.000 | 9.0 | 9.0 | 6.8 | | 8.8 | 8.8 | 6.8 | 8.8 | 8.3 | | 9.0 | | 2.6 | | |
| | .800 | 8.9 | 8.8 | 7.6 | | 8.6 | 8.3 | 7.7 | 8.4 | 7.7 | | 8.0 | 8.3 | 4.0 | | 8.8 |
| | .500 | 9.0 | 8.9 | 7.0 | 9.0 | 6.0 | 9.0 | 8.0 | 9.0 | 5.0 | | 8.0 | 5.0 | 2.3 | 9.0 | 9.0 |
| 2-(5-Isopropyl-5-methyl-4-oxo-2-imidazolin-2-yl)-6-nitro-3-quinolinecarboxylic acid | 1.000 | 9.0 | | 6.0 | 9.0 | 4.0 | 9.0 | 8.0 | 9.0 | 2.0 | 9.0 | 8.0 | 4.0 | | 8.0 | 7.0 |
| | .500 | 9.0 | | 1.0 | 4.0 | 3.0 | 9.0 | 7.0 | 8.0 | 1.0 | | 6.0 | 1.0 | | 7.0 | 3.0 |
| | .250 | | | | | | | | | | | | | | 6.0 | |
| 6-(Difluoromethoxy)-2-(5-isopropyl-5-methyl-4-oxo-2-imidazolin-2-yl)-3-quinolinecarboxylic acid | 1.000 | 9.0 | | 0.0 | 9.0 | 7.0 | 9.0 | 9.0 | 9.0 | 4.0 | | 9.0 | 7.0 | | 9.0 | 9.0 |
| | .500 | 8.0 | | 0.0 | 9.0 | 4.0 | 4.0 | 8.0 | | 3.0 | | 9.0 | 6.0 | | 9.0 | 9.0 |
| | .250 | 8.0 | | 0.0 | | 4.0 | 1.0 | 7.0 | | 1.0 | | 9.0 | 5.0 | | 9.0 | 9.0 |
| 2-(5-Isopropyl-5-methyl-4-oxo-2-imidazolin-2-yl)-8-methoxy-3-quinolinecarboxylic acid | 1.000 | 9.0 | | 7.0 | 9.0 | 6.0 | 2.0 | 3.0 | 8.0 | 9.0 | | 9.0 | 6.0 | | 9.0 | 9.0 |
| | .500 | 7.0 | | 4.0 | 9.0 | 5.0 | 1.0 | 1.0 | 8.0 | 9.0 | | 9.0 | 5.0 | | 9.0 | 9.0 |
| | .250 | 5.0 | | 2.0 | 9.0 | 4.0 | 1.0 | 1.0 | 7.0 | 9.0 | | 9.0 | 5.0 | | 9.0 | 9.0 |

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE, NATO | SOY-BEAN AD | SUN-FLR XXX | S WHEAT ER |
|---|---|---|---|---|---|---|---|---|---|---|---|---|---|---|---|---|
| 2-(5-Isopropyl-5-methyl-4-oxo-2-imidazolin-2-yl)-8-nitro-3-quinoline carboxylic acid | 1.000 | 7.0 | | 0.0 | 8.0 | 0.0 | 0.0 | 2.0 | 0.0 | 0.0 | | 9.0 | 3.0 | 0.0 | 5.0 | 2.0 |
| | .500 | 2.0 | | 0.0 | 2.0 | 0.0 | 0.0 | 1.0 | 0.0 | 0.0 | | 7.0 | 2.0 | 0.0 | 2.0 | 0.0 |
| | .250 | 0.0 | | 0.0 | 0.0 | 0.0 | 0.0 | 1.0 | 0.0 | 0.0 | | 6.0 | 0.0 | 0.0 | 0.0 | 0.0 |
| | .125 | 0.0 | | 0.0 | 0.0 | 0.0 | 0.0 | 1.0 | 0.0 | 0.0 | | 5.0 | 0.0 | 0.0 | 2.0 | 0.0 |
| | .063 | 0.0 | | 0.0 | 0.0 | 0.0 | 0.0 | 1.0 | 0.0 | 0.0 | | 5.0 | 0.0 | 0.0 | 2.0 | 0.0 |
| | .032 | 0.0 | | 0.0 | 0.0 | 0.0 | 0.0 | 1.0 | 0.0 | 0.0 | | 4.0 | 0.0 | 0.0 | 0.0 | 0.0 |
| (−)-2-(5-Isopropyl-5-methyl-4-oxo-2-imidazolin-2-yl)-3-quinolinecarboxylic acid | 1.000 | 8.8 | 9.0 | 7.0 | | 8.8 | 8.3 | 6.8 | 8.0 | 8.8 | | | | | | |
| | .800 | 8.8 | 9.0 | 5.8 | | 8.3 | 8.8 | 6.3 | 8.0 | 8.8 | | | | | | |
| | .500 | 8.5 | 8.8 | 5.8 | | 7.5 | 8.0 | 5.5 | 7.8 | 7.5 | | | | | | |
| | .400 | 8.5 | 8.5 | 5.5 | | 7.3 | 7.8 | 5.3 | 7.8 | 7.8 | | | | | | |
| | .300 | 7.8 | 8.5 | 4.5 | | 7.3 | 7.5 | 4.8 | 7.5 | 8.8 | | | | | | |
| (+)-2-(5-Isopropyl-5-methyl-4-oxo-2-imidazolin-2-yl)-3-quinolinecarboxylic acid | 1.000 | 9.0 | 9.0 | 7.0 | | 8.8 | 8.8 | 8.0 | 9.0 | 8.8 | | | | | | |
| | .800 | 9.0 | 9.0 | 7.3 | | 9.0 | 9.0 | 7.8 | 9.0 | 9.0 | | | | | | |
| | .500 | 9.0 | 9.0 | 6.8 | | 8.8 | 9.0 | 7.0 | 8.8 | 8.8 | | | | | | |
| | .400 | 8.8 | 8.8 | 6.8 | | 8.3 | 9.0 | 7.0 | 7.8 | 8.0 | | | | | | |
| | .300 | 8.8 | 8.8 | 6.8 | | 7.8 | 8.7 | 6.3 | 8.0 | 7.3 | | | | | | |
| | .200 | 8.8 | 9.0 | 6.8 | | 8.3 | 8.3 | 6.0 | 7.5 | 7.3 | | | | | | |
| | .150 | 9.0 | 8.8 | 5.8 | | 8.3 | 8.3 | 5.0 | 7.8 | 7.0 | | | | | | |
| 2-(5-Isopropyl-5- | 1.000 | 8.0 | | 0.0 | 9.0 | 6.0 | 2.0 | 2.0 | 9.0 | 3.0 | | 8.0 | 5.0 | 1.0 | 9.0 | 9.0 |

TABLE I-continued

POST-EMERGENCE TESTS - RATES IN KG/HA

| Compound | Rate | | | | | | | | | | | | | | |
|---|---|---|---|---|---|---|---|---|---|---|---|---|---|---|---|
| methyl-4-oxo-2-imidazolin-2-yl)-6-(trifluoromethyl)-3-quinolinecarboxylic acid | .500 | 6.0 | | 8.0 | 4.0 | 1.0 | 1.0 | 8.0 | 1.0 | 7.0 | 5.0 | 1.0 | 9.0 | 6.0 |
| | .250 | 2.0 | | 7.0 | 1.0 | 0.0 | 1.0 | | 0.0 | 7.0 | 2.0 | 0.0 | 9.0 | 5.0 |
| | .125 | 1.0 | | 3.0 | 0.0 | 0.0 | 0.0 | | 0.0 | 7.0 | 1.0 | 0.0 | 2.0 | 2.0 |
| | .063 | 0.0 | | 0.0 | 0.0 | 0.0 | 0.0 | | 0.0 | 1.0 | 0.0 | 9.0 | 2.0 | 0.0 |
| Ethylammonium 2-(5-isopropyl-5-methyl-4-oxo-2-imidazolin-2-yl)-3-quinoline-carboxylate | 1.290 | 9.0 | | 9.0 | 9.0 | 9.0 | 9.0 | | 9.0 | 9.0 | 9.0 | 9.0 | 9.0 | 9.0 |
| | .645 | 9.0 | | 9.0 | 8.0 | 9.0 | 9.0 | | 9.0 | 9.0 | 9.0 | 3.0 | 9.0 | 9.0 |
| | .323 | 9.0 | | 9.0 | 7.0 | 9.0 | 6.0 | | 9.0 | 9.0 | 9.0 | 3.0 | 9.0 | 6.0 |
| | .161 | 9.0 | | 9.0 | 6.0 | 5.0 | 9.0 | | 3.0 | 9.0 | 9.0 | 2.0 | 9.0 | 4.0 |
| | .091 | 9.0 | | 9.0 | 5.0 | 4.0 | 6.0 | | 2.0 | 9.0 | 9.0 | 1.0 | 9.0 | 2.0 |
| | .040 | 3.0 | | 5.0 | 4.0 | 9.0 | 4.0 | | 1.0 | 9.0 | 9.0 | 5.0 | 8.0 | 0.0 |
| Methylammonium 2-(5-isopropyl-5-methyl-4-oxo-2-imidazolin-2-yl)-3-quinoline-carboxylate | 1.220 | 9.0 | | 9.0 | 9.0 | 9.0 | 9.0 | | 9.0 | 9.0 | 9.0 | 4.0 | 9.0 | 9.0 |
| | .610 | 9.0 | | 9.0 | 8.0 | 9.0 | 7.0 | | 9.0 | 9.0 | 9.0 | 3.0 | 9.0 | 6.0 |
| | .105 | 9.0 | | 9.0 | 8.0 | 9.0 | 6.0 | | 9.0 | 9.0 | 9.0 | 2.0 | 9.0 | 9.0 |
| | .153 | 9.0 | | 9.0 | 7.0 | 6.0 | 6.0 | | 5.0 | 9.0 | 9.0 | 1.0 | 9.0 | 7.0 |
| | .076 | 5.0 | | 5.0 | 7.0 | 7.0 | 6.0 | | 2.0 | 9.0 | 9.0 | 0.0 | 9.0 | 4.0 |
| | .038 | 3.0 | | 3.0 | 4.0 | 9.0 | 2.0 | | 1.0 | 9.0 | 9.0 | 7.0 | 9.0 | 4.0 |
| Dimethylammonium 2-(5-isopropyl-5-methyl-4-oxo-2-imidazolin-2-yl)-3-quinoline-carboxylate | 1.300 | 9.0 | | 9.0 | 9.0 | 9.0 | 9.0 | | 9.0 | 9.0 | 9.0 | 4.0 | 9.0 | 9.0 |
| | .650 | 9.0 | | 9.0 | 8.0 | 9.0 | 6.0 | | 9.0 | 9.0 | 9.0 | 2.0 | 9.0 | 9.0 |
| | .323 | 9.0 | | 9.0 | 7.0 | 9.0 | 9.0 | | 9.0 | 9.0 | 9.0 | 3.0 | 9.0 | 8.0 |
| | .163 | 9.0 | | 9.0 | 7.0 | 5.0 | 4.0 | | 4.0 | 9.0 | 9.0 | 1.0 | 9.0 | 8.0 |
| | .021 | 8.0 | | 8.0 | 6.0 | 5.0 | 6.0 | | 3.0 | 9.0 | 8.0 | 3.0 | 9.0 | 8.0 |
| | .041 | 8.0 | | 7.0 | 5.0 | 5.0 | 4.0 | | 2.0 | 9.0 | 9.0 | 1.0 | 9.0 | 2.0 |
| Octylammonium 2-(5-isopropyl-5-methyl-4-oxo-2-imidazolin-2-yl)-3-quinoline-carboxylate | 1.570 | 9.0 | | 9.0 | 8.0 | 8.0 | 7.0 | | 9.0 | 9.0 | 9.0 | 3.0 | 9.0 | 9.0 |
| | .785 | 9.0 | | 9.0 | 8.0 | 8.0 | 8.0 | | 5.0 | 9.0 | 9.0 | 2.0 | 9.0 | 5.0 |
| | .323 | 9.0 | | 9.0 | 8.0 | 7.0 | 6.0 | | 4.0 | 9.0 | 9.0 | 1.0 | 9.0 | 6.0 |
| | .176 | 8.0 | | 8.0 | 6.0 | 5.0 | 6.0 | | 2.0 | 9.0 | 7.0 | 0.0 | 9.0 | 4.0 |
| | .078 | 8.0 | | 8.0 | 3.0 | 8.0 | 3.0 | | 1.0 | 9.0 | 6.0 | 1.0 | 8.0 | 2.0 |
| | .049 | 2.0 | 9.0 | 7.0 | 7.0 | | 6.0 | | 9.0 | 9.0 | 9.0 | 1.0 | 8.0 | 2.0 |
| 2-(5-Isopropyl-5-methyl-4-oxo-2-imidazolin-2-yl)-6-methoxy-3-quinolinecarboxylic acid | 8.000 | 9.0 | | 9.0 | 2.0 | 0.0 | 6.0 | 9.0 | 3.0 | 9.0 | 9.0 | 6.0 | 9.0 | 6.0 |
| | 1.000 | 9.0 | | 9.0 | 8.0 | 9.0 | 6.0 | 7.0 | 3.0 | 9.0 | 7.0 | 5.0 | 9.0 | 4.0 |
| | .500 | 9.0 | | 9.0 | 7.0 | 6.0 | 2.0 | 7.0 | 3.0 | 9.0 | 9.0 | 5.0 | 9.0 | 4.0 |
| | .250 | 6.0 | | 9.0 | 5.0 | 0.0 | 0.0 | 3.0 | | 9.0 | 8.0 | 3.0 | 8.0 | 4.0 |
| | .125 | 2.0 | | 7.0 | 3.0 | 6.0 | 0.0 | 1.0 | 1.0 | 4.0 | 5.0 | 1.0 | 5.0 | 3.0 |
| | .063 | 1.0 | | 6.0 | 1.0 | 0.0 | 0.0 | 0.0 | 0.0 | 9.0 | 4.0 | 0.0 | 4.0 | 3.0 |
| 2-(5-Isopropyl-5-methyl-4-oxo-2-imidazoline-2-yl)-8-methoxy-7-nitro-3-quinolinecarboxylic acid | 1.000 | 0.0 | | 0.0 | 0.0 | 0.0 | 0.0 | 0.0 | 0.0 | 9.0 | 0.0 | 0.0 | 2.0 | 0.0 |
| | .500 | 0.0 | | 0.0 | 0.0 | 0.0 | 0.0 | 0.0 | 0.0 | 9.0 | 0.0 | 0.0 | 2.0 | 0.0 |
| Benzyl 2-(5-isopropyl-5-methyl-4-oxo-2-imidazolin-2-yl)-3-quinoline-carboxylate | 1.000 | 9.0 | | 9.0 | 6.0 | 6.0 | 9.0 | 9.0 | 3.0 | 9.0 | 7.0 | 3.0 | 9.0 | 4.0 |
| | .500 | 9.0 | | 8.0 | 5.0 | 4.0 | 6.0 | 8.0 | 2.0 | 9.0 | 7.0 | 3.0 | 8.0 | 4.0 |
| | .250 | 9.0 | | 5.0 | 5.0 | 4.0 | 3.0 | 2.0 | 0.0 | 9.0 | 5.0 | 2.0 | 8.0 | 3.0 |
| | .125 | 9.0 | | 8.0 | 2.0 | 3.0 | 3.0 | 0.0 | 0.0 | 9.0 | 4.0 | 1.0 | 6.0 | 1.0 |
| | .063 | 6.0 | | 3.0 | 2.0 | 1.0 | 2.0 | 0.0 | 0.0 | 9.0 | 2.0 | 4.0 | 4.0 | 1.0 |
| 2-(5-Isopropyl-5-methyl-4-oxo-2-imidazolin-2-yl)-5-methyl-3-quinolinecarboxylic acid | 1.000 | | | 9.0 | 9.0 | 9.0 | 9.0 | 7.0 | 9.0 | 9.0 | 9.0 | 4.0 | 7.0 | 9.0 |
| | .500 | 9.0 | | 9.0 | 4.0 | 4.0 | 3.0 | 6.0 | 3.0 | 9.0 | 8.0 | 4.0 | 7.0 | 3.0 |
| | .250 | 9.0 | | 9.0 | 2.0 | 3.0 | 2.0 | 5.0 | 1.0 | 9.0 | 7.0 | 2.0 | 6.0 | 3.0 |
| | .125 | 5.0 | | 7.0 | 1.0 | 2.0 | 3.0 | 1.0 | 1.0 | 9.0 | 4.0 | 2.0 | 6.0 | 3.0 |
| | .063 | 4.0 | | 6.0 | 0.0 | 1.0 | 2.0 | 1.0 | 1.0 | 9.0 | 4.0 | 2.0 | 2.0 | 2.0 |

TABLE I-continued
POST-EMERGENCE TESTS - RATES IN KG/HA

| Compound | Rate | | | | | | | | | | | | |
|---|---|---|---|---|---|---|---|---|---|---|---|---|---|
| Methyl 2-[(1-carbamoyl-1,2-dimethyl-propyl)-carbamoyl]-3-quinolinecarboxylate | 4.000 | 9.0 | 7.0 | 0.0 | 4.0 | 0.0 | 0.0 | 1.0 | 8.0 | 9.0 | 3.0 | 2.0 | 7.0 | 5.0 |
| | 1.000 | 2.0 | 5.0 | 0.0 | 0.0 | 0.0 | 0.0 | 0.0 | 1.0 | 3.0 | 1.0 | 1.0 | 2.0 | 3.0 |
| | .500 | 1.0 | 2.0 | 0.0 | 0.0 | 0.0 | 0.0 | 0.0 | 0.0 | 1.0 | 0.0 | 0.0 | 1.0 | 3.0 |
| Butyl 2-(5-isopropyl-5-methyl-4-oxo-2-imidazolin-2-yl)-3-quinolinecarboxylate | 4.000 | 8.0 | 9.0 | 7.0 | 9.0 | 9.0 | 4.0 | 2.0 | 9.0 | 4.0 | 6.0 | 9.0 | 7.0 | 1.0 |
| | 1.000 | 3.0 | 6.0 | 2.0 | 3.0 | 7.0 | 3.0 | 0.0 | 0.0 | 2.0 | 0.0 | 5.0 | 7.0 | 0.0 |
| | .500 | 0.0 | 6.0 | 2.0 | 0.0 | 2.0 | 2.0 | 0.0 | 0.0 | 3.0 | 0.0 | 0.0 | 7.0 | 0.0 |
| 2-(5-Isopropyl-5-methyl-4-oxo-2-imidazolin-2-yl)-3-quinolinecarboxylic acid hydrochloride | 4.000 | 9.0 | 8.0 | 8.0 | 9.0 | 9.0 | 9.0 | 9.0 | 9.0 | 9.0 | 9.0 | 5.0 | 9.0 | 9.0 |
| | 1.000 | 9.0 | 8.0 | 9.0 | 9.0 | 9.0 | 9.0 | 9.0 | 9.0 | 9.0 | 9.0 | 4.0 | 9.0 | 9.0 |
| | .500 | 9.0 | 9.0 | 7.0 | 9.0 | 7.0 | 9.0 | 7.0 | 9.0 | 9.0 | 9.0 | 4.0 | 9.0 | 9.0 |
| | .250 | 9.0 | 9.0 | 7.0 | 9.0 | 6.0 | 9.0 | 5.0 | 8.0 | 9.0 | 9.0 | 3.0 | 9.0 | 9.0 |
| | .125 | 9.0 | 8.0 | 5.0 | 8.0 | 5.0 | 8.0 | 5.0 | 5.0 | 9.0 | 9.0 | 3.0 | 9.0 | 9.0 |
| 5-Chloro-2-(5-isopropyl-5-methyl-4-oxo-2-imidazolin-2-yl)-3-quinolinecarboxylic acid | 4.000 | 9.0 | 9.0 | 8.0 | 9.0 | 9.0 | 8.0 | 9.0 | 8.0 | 8.0 | 9.0 | 4.0 | 7.0 | 9.0 |
| | 1.000 | 9.0 | 7.0 | 1.0 | 9.0 | 3.0 | 4.0 | 0.0 | 3.0 | 5.0 | 9.0 | 4.0 | 7.0 | 9.0 |
| | .500 | 9.0 | 7.0 | 0.0 | 9.0 | 2.0 | 4.0 | 0.0 | 2.0 | 5.0 | 9.0 | 3.0 | 7.0 | 9.0 |
| | .250 | 9.0 | 5.0 | 0.0 | 9.0 | 0.0 | 3.0 | 0.0 | 1.0 | 3.0 | 9.0 | 3.0 | 7.0 | 9.0 |
| | .125 | 4.0 | 4.0 | 0.0 | 9.0 | 0.0 | 2.0 | 0.0 | 0.0 | 3.0 | 9.0 | 2.0 | 5.0 | 9.0 |
| Tallowammonium 2-(5-isopropyl-5-methyl-4-oxo-2-imidazolin-2-yl)-3-quinolinecarboxylate | 2.080 | 9.0 | | 7.0 | 9.0 | 9.0 | 9.0 | 7.0 | | 9.0 | 9.0 | 4.0 | 9.0 | 9.0 |
| | 1.040 | 9.0 | | 7.0 | 9.0 | 9.0 | 9.0 | 9.0 | | 9.0 | 7.0 | 4.0 | 9.0 | 9.0 |
| | .520 | 9.0 | | 7.0 | 9.0 | 7.0 | 9.0 | 9.0 | | 9.0 | 7.0 | 3.0 | 9.0 | 9.0 |
| | .260 | 9.0 | | 6.0 | 9.0 | 6.0 | 9.0 | 9.0 | | 9.0 | 5.0 | 2.0 | 9.0 | 9.0 |
| | .130 | 9.0 | | 5.0 | 8.0 | 5.0 | 7.0 | 8.0 | | 9.0 | 9.0 | 1.0 | 9.0 | 8.0 |
| | .065 | 9.0 | | 4.0 | 3.0 | 4.0 | 6.0 | 3.0 | | 9.0 | 7.0 | 0.0 | 9.0 | 6.0 |
| Isopropylammonium 2-(5-isopropyl-5-methyl-4-oxo-2-imidazolin-2-yl)-3-quinolinecarboxylate | 1.320 | 9.0 | | 7.0 | 9.0 | 9.0 | 9.0 | 9.0 | | 9.0 | 9.0 | 0.0 | 9.0 | 9.0 |
| | .660 | 9.0 | | 7.0 | 9.0 | 8.0 | 9.0 | 9.0 | | 9.0 | 9.0 | 6.0 | 9.0 | 9.0 |
| | .330 | 9.0 | | 7.0 | 9.0 | 6.0 | 9.0 | 7.0 | | 9.0 | 9.0 | 3.0 | 9.0 | 9.0 |
| | .165 | 9.0 | | 7.0 | 9.0 | 6.0 | 9.0 | 8.5 | | 9.0 | 9.0 | 2.0 | 9.0 | 9.0 |
| | .083 | 9.0 | | 5.0 | 9.0 | 6.0 | 9.0 | 7.0 | | 9.0 | 9.0 | 2.0 | 9.0 | 9.0 |
| | .041 | 5.0 | | 3.0 | 8.0 | 7.0 | 9.0 | 5.0 | | 9.0 | 9.0 | 1.0 | 9.0 | 6.0 |
| Sodium 2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 9.0 | 8.0 | 9.0 | 9.0 | 0.0 | 9.0 | 9.0 |
| | 1.320 | 9.0 | | 9.0 | 9.0 | 9.0 | 9.0 | 8.5 | 8.5 | 9.0 | 9.0 | 5.0 | 9.0 | 9.0 |
| | 1.000 | 9.0 | | 8.0 | 9.0 | 9.0 | 9.0 | 9.0 | 9.0 | 9.0 | 9.0 | 5.0 | 9.0 | 9.0 |
| | .660 | 9.0 | | 7.0 | 9.0 | 8.0 | 7.5 | 9.0 | | 6.0 | 9.0 | 5.0 | 9.0 | 6.0 |
| | .500 | 9.0 | | 7.0 | 9.0 | 6.0 | 8.0 | 9.0 | | 7.0 | 9.0 | 3.0 | 9.0 | 4.0 |
| | .330 | 9.0 | | 7.0 | 9.0 | 7.0 | 9.0 | 8.0 | | 8.0 | 8.0 | 5.0 | 9.0 | 2.0 |
| | .250 | 8.0 | | 7.0 | 9.0 | 5.0 | 6.0 | 5.0 | | 9.0 | 9.0 | 2.0 | 9.0 | 9.0 |
| 2-(5-Isopropyl-5-methyl-4-oxo-2-imidazolin-2-yl)-3-quinoline-carboxaldehyde | 4.000 | 9.0 | 7.0 | 8.0 | 9.0 | 9.0 | 9.0 | 5.0 | 9.0 | 9.0 | 9.0 | 5.0 | 9.0 | 9.0 |
| | 1.000 | 6.0 | 6.0 | 9.0 | 9.0 | 9.0 | 8.0 | 8.0 | 8.0 | 9.0 | 7.0 | 4.0 | 9.0 | 7.0 |
| 2-(5-Isopropyl-5-methyl-4-oxo-2-imidazolin-2-yl)-6-nitro-3-quinolinecarboxylic acid | 1.000 | 9.0 | | 7.0 | 9.0 | 9.0 | 8.0 | 8.0 | 9.0 | 8.0 | 5.0 | 3.0 | 8.0 | 9.0 |
| | .500 | 9.0 | | 6.0 | 9.0 | 9.0 | 8.0 | 8.0 | 9.0 | 8.0 | 4.0 | 1.0 | 7.0 | 7.0 |
| | .250 | 9.0 | | 1.0 | 9.0 | 4.0 | 3.0 | 7.0 | 8.0 | 6.0 | 1.0 | 1.0 | 6.0 | 3.0 |
| | .125 | 4.0 | | 0.0 | 2.0 | 2.0 | 1.0 | 0.0 | | 7.0 | 1.0 | 1.0 | 5.0 | 2.0 |
| | .063 | 1.0 | | 0.0 | 0.0 | 1.0 | 1.0 | 0.0 | | 1.0 | 1.0 | 1.0 | 5.0 | 1.0 |
| 2-(5-Isopropyl-5-methyl-4-oxo- | 1.000 | 0.0 | | 0.0 | 0.0 | 1.0 | 2.0 | 0.0 | 0.0 | 0.0 | 3.0 | 1.0 | 7.0 | 0.0 |
| | .500 | 0.0 | | 0.0 | 0.0 | 0.0 | 1.0 | 2.0 | 9.0 | 0.0 | 2.0 | 0.0 | 5.0 | 0.0 |

TABLE I-continued

POST-EMERGENCE TESTS - RATES IN KG/HA

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE NATO | SOY-BEAN WI | SUN-FLR XXX | S WHEAT ER |
|---|---|---|---|---|---|---|---|---|---|---|---|---|---|---|---|---|
| 2-imidazolin-2-yl)-6,8-dimethyl-3-quinolinecarboxylic acid | .250 | | | | 0.0 | 0.0 | 1.0 | 0.0 | 3.0 | 0.0 | | 4.0 | 0.0 | 0.0 | 3.0 | 0.0 |
| 7-Chloro-2-(5-isopropyl-5-methyl-4-oxo-2-imidazolin-2-yl)-3-quinolinecarboxylic acid | 4.000 | 9.0 | 9.0 | 4.0 | 9.0 | 9.0 | 9.0 | 8.0 | 7.0 | 8.0 | | 9.0 | 9.0 | 5.0 | 9.0 | 7.0 |
| | 1.000 | 9.0 | 8.0 | 4.0 | 9.0 | 2.0 | 4.0 | 6.0 | 1.0 | 3.0 | | 9.0 | 8.0 | 4.0 | 9.0 | 5.0 |
| | .500 | 9.0 | 7.0 | 1.0 | 9.0 | 1.0 | 3.0 | 1.0 | 0.0 | 1.0 | | 9.0 | 7.0 | 3.0 | 9.0 | 4.0 |
| | .250 | 3.0 | 6.0 | 1.0 | 7.0 | 0.0 | 0.0 | 0.0 | 0.0 | 0.0 | | 9.0 | 6.0 | 3.0 | 7.0 | 3.0 |
| | .125 | 0.0 | 3.0 | 1.0 | 1.0 | 0.0 | 0.0 | 0.0 | 0.0 | 0.0 | | 8.0 | 3.0 | 2.0 | 5.0 | 2.0 |
| Ammonium-2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 9.0 | 8.0 | 9.0 | | 9.0 | 9.0 | 6.0 | 9.0 | 9.0 |
| | 1.230 | 9.0 | | 7.0 | 9.0 | 8.0 | 9.0 | 8.0 | | 8.0 | | 9.0 | 9.0 | 4.0 | 9.0 | 9.0 |
| | 1.000 | 9.0 | 9.0 | 8.5 | 9.0 | 9.0 | 9.0 | 8.0 | 8.0 | 8.0 | | 9.0 | 9.0 | 5.0 | 9.0 | 9.0 |
| | .615 | 9.0 | | 5.0 | 9.0 | 9.0 | 9.0 | 8.0 | | 8.0 | | 9.0 | 9.0 | 3.0 | 9.0 | 9.0 |
| | .500 | 9.0 | | 9.0 | 9.0 | 9.0 | 9.0 | 9.0 | 9.0 | 9.0 | | 9.0 | 8.0 | 6.0 | 9.0 | 9.0 |
| | .308 | 7.0 | | 7.0 | 9.0 | 7.0 | 5.0 | 9.0 | | 6.0 | | 9.0 | 7.0 | 3.0 | 9.0 | 9.0 |
| | .250 | 9.0 | | 8.0 | 9.0 | 9.0 | 6.0 | 9.0 | 9.0 | 8.0 | | 9.0 | 9.0 | 5.0 | 9.0 | 6.0 |
| | .154 | 9.0 | | 6.0 | 9.0 | 7.0 | 4.0 | 7.0 | | 8.0 | | 9.0 | 4.0 | 2.0 | 7.0 | 3.0 |
| Ethyl 2-(5-isopropyl-5-methyl-4-oxo-2-imidazolin-2-yl)-3-quinolinecarboxylate | 4.000 | 9.0 | 8.0 | 7.0 | 9.0 | 6.0 | 6.0 | 7.0 | 7.0 | 7.0 | | 9.0 | 4.0 | 5.0 | 7.0 | 7.0 |
| | 1.000 | 7.0 | 5.0 | 3.0 | 8.0 | 4.0 | 4.0 | 3.0 | 7.0 | 3.0 | | 4.0 | 3.0 | 5.0 | 7.0 | 3.0 |
| | .500 | 2.0 | 5.0 | 3.0 | 8.0 | | 4.0 | 3.0 | 0.0 | 3.0 | | 4.0 | 3.0 | 3.0 | 6.0 | 3.0 |
| | .250 | | 5.0 | 1.0 | 8.0 | 1.0 | 1.0 | 1.0 | 0.0 | 1.0 | | 3.0 | 3.0 | 3.0 | 6.0 | 3.0 |
| 7-Ethoxy-2-(5-isopropyl-5-methyl-4-oxo-2-imidazolin-2-yl)-3-quinolinecarboxylic acid | 8.000 | 9.0 | 7.0 | 9.0 | 9.0 | 0.0 | 7.0 | 6.0 | 9.0 | | | 9.0 | 1.0 | 6.0 | 2.0 | 5.0 |
| | 1.000 | 3.0 | 0.0 | 9.0 | 0.0 | 0.0 | 1.0 | 3.0 | 0.0 | | | 9.0 | 3.0 | 5.0 | 1.0 | 3.0 |
| | .500 | 2.0 | 0.0 | 9.0 | 0.0 | 0.0 | 1.0 | 3.0 | 0.0 | | | 6.0 | | 4.0 | 0.0 | 3.0 |
| | .250 | 0.0 | 0.0 | 9.0 | 0.0 | 0.0 | 0.0 | 8.0 | 0.0 | | | 4.0 | 2.0 | 4.0 | 0.0 | 3.0 |
| | .125 | 0.0 | 0.0 | 6.0 | 0.0 | 0.0 | 0.0 | 6.0 | 0.0 | | | 2.0 | 0.0 | 3.0 | 0.0 | 2.0 |
| | .063 | 0.0 | 0.0 | 5.0 | 0.0 | 0.0 | | 3.0 | 0.0 | | | 0.0 | 0.0 | 2.0 | 0.0 | 1.0 |
| | .032 | 0.0 | | 3.0 | 0.0 | 0.0 | | 2.0 | 0.0 | | | 6.0 | 0.0 | 2.0 | 0.0 | 1.0 |
| 2-(5-Isopropyl-5-methyl-4-oxo-2-imidazolin-2-yl)-4-methyl-3-quinolinecarboxylic acid | 1.000 | 3.0 | | 3.0 | 0.0 | 1.0 | 9.0 | 9.0 | 0.0 | 9.0 | | 6.0 | 3.0 | 1.0 | 9.0 | 0.0 |
| | .500 | 1.0 | | 1.0 | 0.0 | 0.0 | 4.0 | 8.0 | 0.0 | 3.0 | | 3.0 | 3.0 | 1.0 | 7.0 | 0.0 |
| | .250 | 1.0 | | 0.0 | 0.0 | 0.0 | | 6.0 | 0.0 | 1.0 | | 3.0 | 2.0 | 0.0 | 5.0 | 0.0 |
| | .125 | 0.0 | | 0.0 | 0.0 | 0.0 | 0.0 | 6.0 | 0.0 | 1.0 | | 3.0 | 1.0 | 0.0 | 4.0 | 0.0 |
| | .063 | 0.0 | | 0.0 | 0.0 | 0.0 | 0.0 | 2.0 | 0.0 | 0.0 | | 3.0 | 1.0 | 0.0 | 4.0 | 0.0 |
| Diisopropylammonium 2-(5-isopropyl-5-methyl-4-oxo-2-imidazolin-2-yl)-3-quinolinecarboxylate | 4.000 | 9.0 | | 9.0 | 9.0 | 9.0 | 9.0 | 9.0 | 9.0 | 9.0 | | 9.0 | 9.0 | | 9.0 | |
| | 1.500 | 9.0 | | 7.0 | 9.0 | 9.0 | 9.0 | 6.0 | | 9.0 | | 9.0 | 9.0 | | 9.0 | |
| | 1.000 | 9.0 | 8.0 | 7.5 | 9.0 | 9.0 | 9.0 | 8.5 | 8.5 | 8.0 | | 9.0 | 8.5 | | 9.0 | |
| | .750 | 9.0 | | 7.0 | 9.0 | 9.0 | 9.0 | 8.0 | | 9.0 | | 9.0 | 9.0 | | 9.0 | |
| | .500 | 9.0 | | 7.0 | 9.0 | 9.0 | 9.0 | 8.0 | 9.0 | 8.0 | | 9.0 | 9.0 | | 9.0 | |
| | .375 | 9.0 | | 7.0 | 9.0 | 9.0 | 9.0 | 6.0 | | 8.0 | | 8.0 | 8.0 | | 9.0 | |
| Calcium 2-(5-isopropyl-5-methyl-4-oxo-2-imidazolin-2-yl)-3-quinolinecarboxylate | 4.000 | 9.0 | 9.0 | 9.0 | 9.0 | 9.0 | 8.5 | 9.0 | 9.0 | 9.0 | | 9.0 | 9.0 | | 9.0 | |
| | 1.000 | 9.0 | 8.0 | 9.0 | 9.0 | 9.0 | 9.0 | 8.0 | 9.0 | 8.0 | | 9.0 | 9.0 | | 9.0 | |
| | .500 | 9.0 | | 8.0 | 9.0 | 9.0 | 9.0 | 8.0 | 8.0 | 6.0 | | 9.0 | 9.0 | | 9.0 | |
| | .250 | 8.0 | | 7.0 | 9.0 | 9.0 | 4.0 | 2.0 | 6.0 | 4.0 | | 9.0 | 7.0 | | 9.0 | |
| | .125 | 8.0 | | 7.0 | 9.0 | 8.0 | 4.0 | 1.0 | 4.0 | 2.0 | | 9.0 | 7.0 | | 9.0 | |
| | .063 | 8.0 | | 2.0 | 7.0 | 7.0 | 3.0 | 1.0 | 4.0 | 2.0 | | 9.0 | 6.0 | | 9.0 | |
| | .032 | 8.0 | | 4.0 | 7.0 | 6.0 | 5.0 | 7.0 | 4.0 | 3.0 | | 7.5 | 5.5 | 2.5 | 9.0 | |
| 6-Chloro-2-(5-isopropyl-5-methyl-4- | 1.000 | 9.0 | | 4.0 | 8.5 | 6.0 | 5.0 | 6.0 | 9.0 | 3.0 | | 7.5 | 5.5 | 2.5 | 9.0 | |
| | .500 | 9.0 | | 1.5 | 8.5 | 6.0 | 4.5 | 6.0 | 9.0 | 2.0 | | 6.0 | 4.5 | 2.0 | 8.5 | |

TABLE I-continued

POST-EMERGENCE TESTS - RATES IN KG/HA

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE, NATO | SOY-BEAN AD | SUN-FLR XXX | S WHEAT ER |
|---|---|---|---|---|---|---|---|---|---|---|---|---|---|---|---|---|
| oxo-2-imidazolin-2-yl)-3-quinoline-carboxylic acid | .250 | 8.5 | | 0.5 | 8.5 | 5.5 | 1.0 | 4.5 | 7.0 | 1.0 | | 2.5 | 3.0 | 2.0 | 7.5 | 6.0 |
| | .125 | 6.5 | | 0.0 | 7.5 | 2.5 | 0.0 | 3.0 | 6.5 | 0.0 | | 0.5 | 3.0 | 1.0 | 8.0 | 5.0 |
| | .063 | 2.5 | | 0.0 | 6.0 | 1.5 | 0.0 | 0.5 | 6.0 | 0.0 | | 0.5 | 2.5 | 0.5 | 6.0 | 5.0 |
| | .032 | 1.0 | | 0.0 | 4.5 | 1.0 | 0.0 | 0.0 | 2.5 | 0.0 | | 0.5 | 2.0 | 0.0 | 3.0 | 5.0 |
| Tallowammonium 2-(5-isopropyl)-5-methyl-4-oxo-2-imidazolin-2-yl)-3-quinolinecar-boxylate | 2.000 | 9.0 | | 7.0 | 9.0 | 9.0 | 9.0 | 7.0 | | 9.0 | | 9.0 | 9.0 | | 9.0 | 4.0 |
| | 1.040 | 9.0 | | 7.0 | 9.0 | 9.0 | 9.0 | 9.0 | | 9.0 | | 9.0 | 9.0 | | 9.0 | 4.0 |
| | .520 | 9.0 | | 7.0 | 9.0 | 7.0 | 9.0 | 8.0 | | 6.0 | | 9.0 | 8.0 | | 9.0 | |
| | .260 | 9.0 | | 6.0 | 8.0 | 6.0 | 7.0 | 8.0 | | 3.0 | | 9.0 | 9.0 | | 9.0 | |
| | .130 | 9.0 | | 5.0 | 9.0 | 5.0 | 6.0 | 0.0 | | 2.0 | | 9.0 | 9.0 | | 9.0 | |
| | .065 | 9.0 | | 4.0 | 3.0 | 4.0 | 2.0 | 0.0 | | 1.0 | | 9.0 | 7.0 | | 9.0 | |
| 5-Bromo-2-(5-isopropyl-5-methyl-4-oxo-2-imidazolin-2-yl)-3-quinoline-carboxylic acid | 1.000 | 9.0 | | 1.0 | 9.0 | 8.0 | 4.0 | 4.0 | 2.0 | 2.0 | | 9.0 | 8.0 | 2.0 | 2.0 | 9.0 |
| | .500 | 6.0 | | 0.0 | 9.0 | 7.0 | 4.0 | 3.0 | | 1.0 | | 9.0 | 6.0 | 0.0 | 2.0 | 9.0 |
| | .250 | 3.0 | 9.0 | 0.0 | 8.0 | 3.0 | | 1.0 | 0.0 | 0.0 | | 9.0 | 6.0 | 0.0 | 1.0 | 9.0 |
| | .125 | 2.0 | 3.0 | 0.0 | 7.0 | 1.0 | 0.0 | 0.0 | 0.0 | 0.0 | | 9.0 | 6.0 | 0.0 | 1.0 | 9.0 |
| | .063 | 0.0 | 1.0 | 0.0 | 5.0 | 0.0 | 0.0 | 1.0 | 0.0 | 0.0 | | 9.0 | 2.0 | 0.0 | 1.0 | 8.0 |
| | .032 | 0.0 | 0.0 | 0.0 | 5.0 | 0.0 | 0.0 | 0.0 | 0.0 | 0.0 | | 9.0 | 2.0 | 0.0 | 0.0 | 8.0 |
| 8-Chloro-2-(5-isopropyl-5-methyl-4-oxo-2-imidazolin-2-yl)-3-quinoline-carboxylic acid | 5.000 | 9.0 | 9.0 | 9.0 | 9.0 | 9.0 | 8.0 | 9.0 | 9.0 | 7.0 | | 9.0 | 9.0 | 7.0 | 3.0 | 9.0 |
| | 1.000 | 8.0 | 3.0 | 6.0 | 7.0 | 4.0 | 5.0 | 9.0 | 7.0 | 3.0 | | 9.0 | 8.0 | 4.0 | 1.0 | 9.0 |
| | .500 | 2.0 | 1.0 | 3.0 | 5.0 | 3.0 | 3.0 | 8.0 | 5.0 | 0.0 | | 7.0 | 7.0 | 3.0 | 0.0 | 9.0 |
| | .250 | 0.0 | 0.0 | 1.0 | 2.0 | 0.0 | 1.0 | 8.0 | 4.0 | 0.0 | | 7.0 | 5.0 | 3.0 | 0.0 | 8.0 |
| | .125 | 0.0 | 0.0 | 0.0 | 1.0 | 0.0 | 0.0 | 3.0 | 4.0 | 0.0 | | 6.0 | 4.0 | 2.0 | 0.0 | 8.0 |
| | .063 | 0.0 | 0.0 | 0.0 | 0.0 | 0.0 | 0.0 | 2.0 | 2.0 | 0.0 | | 6.0 | 0.0 | 2.0 | 0.0 | 8.0 |
| | .032 | 0.0 | 0.0 | 0.0 | 0.0 | 0.0 | 0.0 | 0.0 | 0.0 | 0.0 | | 6.0 | 0.0 | 0.0 | 0.0 | 8.0 |
| 2-(5-Isopropyl-5-methyl-4-oxo-2-imidazolin-2-yl)-4-methoxy-3-quinolinecarboxylic acid | 8.000 | 9.0 | 9.0 | 7.0 | 7.0 | 5.0 | 0.0 | 5.0 | 8.0 | 7.0 | | 9.0 | 2.0 | 3.0 | 9.0 | 4.0 |
| | 1.000 | 1.0 | | 4.0 | 4.0 | 7.0 | 0.0 | 9.0 | 9.0 | 3.0 | | 9.0 | 2.0 | 2.0 | 9.0 | 3.0 |
| | .500 | 0.0 | | 1.0 | 4.0 | 7.0 | 0.0 | 7.0 | 7.0 | 0.0 | | 5.0 | 2.0 | 0.0 | 9.0 | 3.0 |
| | .250 | 0.0 | | 0.0 | 2.0 | 7.0 | 0.0 | 6.0 | 6.0 | 0.0 | | 2.0 | 1.0 | 0.0 | 9.0 | 3.0 |
| | .125 | 0.0 | | 0.0 | 1.0 | 3.0 | 0.0 | 5.0 | 3.0 | 0.0 | | 1.0 | 0.0 | 0.0 | 9.0 | 2.0 |
| | .063 | 0.0 | | 0.0 | 0.0 | 0.0 | 0.0 | 2.0 | 0.0 | 5.0 | | 1.0 | 0.0 | 0.0 | 2.0 | 2.0 |
| | .032 | 0.0 | | 0.0 | 0.0 | 0.0 | 0.0 | 1.0 | 0.0 | 0.0 | | 1.0 | 0.0 | 0.0 | 2.0 | 2.0 |
| 4-Hydroxy-2-(5-isopropyl-5-methyl-4-oxo-2-imidazolin-2-yl)-3-quinoline-carboxylic acid hydrochloride | 8.000 | 9.0 | 7.0 | 1.0 | 8.0 | 5.0 | 0.0 | 7.0 | 9.0 | 5.0 | | 4.0 | 2.0 | 1.0 | 9.0 | 7.0 |
| | 1.000 | 0.0 | | 0.0 | 2.0 | 0.0 | | 3.0 | 7.0 | 0.0 | | 2.0 | 1.0 | 1.0 | 9.0 | 3.0 |
| | .500 | 0.0 | | 0.0 | 2.0 | 0.0 | | 2.0 | 7.0 | 0.0 | | 2.0 | 1.0 | 0.0 | 6.0 | 3.0 |
| | .250 | 0.0 | | 0.0 | 2.0 | 0.0 | 0.0 | 1.0 | 7.0 | 0.0 | | 2.0 | 0.0 | 0.0 | 6.0 | 3.0 |
| 2-(5-Isopropyl-5-methyl-4-oxo-2-imidazolin-2-yl)-6-methyl-3-quinolinecarboxylic acid | .500 | 8.0 | | 1.0 | 9.0 | 8.0 | 9.0 | 3.0 | 7.0 | 6.0 | | 9.0 | 9.0 | 3.0 | 9.0 | 8.0 |
| | .250 | 8.0 | | 1.0 | 4.0 | 9.0 | 9.0 | 2.0 | 7.0 | 4.0 | | 9.0 | 9.0 | 4.0 | 9.0 | 4.0 |
| | .125 | 7.0 | | 0.0 | 0.0 | 7.0 | 3.0 | 1.0 | 0.0 | 0.0 | | 6.0 | 8.0 | 3.0 | 9.0 | 3.0 |
| | .063 | 4.0 | | 0.0 | 4.0 | 4.0 | 2.0 | 3.0 | 0.0 | 0.0 | | 6.0 | 6.0 | 0.0 | 9.0 | 1.0 |
| | .032 | 2.0 | | 0.0 | 0.0 | 0.0 | 0.0 | 1.0 | 0.0 | 0.0 | | 4.0 | 4.0 | 0.0 | 5.0 | 0.0 |
| Methyl 2-(5-isopropyl-5-methyl-4-oxo-2-imidazolin-2-yl)-7-methyl-3-quinolinecarboxylate | 1.000 | 9.0 | | 0.0 | 0.0 | 0.0 | 3.0 | 3.0 | 0.0 | 2.0 | | 7.0 | 3.0 | 2.0 | 4.0 | 0.0 |
| | .500 | 7.0 | | 0.0 | 0.0 | 0.0 | 0.0 | 0.0 | 0.0 | 0.0 | | 7.0 | 1.0 | 1.0 | 0.0 | 0.0 |
| | .250 | 5.0 | | 0.0 | 0.0 | 0.0 | 0.0 | 1.0 | 0.0 | 0.0 | | 2.0 | 0.0 | 0.0 | 0.0 | 0.0 |
| | .125 | 1.0 | | 0.0 | 0.0 | 0.0 | 0.0 | 0.0 | 0.0 | 0.0 | | 0.0 | 0.0 | 0.0 | 0.0 | 0.0 |
| | .063 | 0.0 | | 0.0 | 0.0 | 0.0 | 0.0 | 0.0 | 0.0 | 0.0 | | 0.0 | 0.0 | 0.0 | 0.0 | 0.0 |
| | .032 | 0.0 | | 0.0 | 0.0 | 2.0 | 0.0 | 0.0 | 0.0 | 0.0 | | 0.0 | 0.0 | 0.0 | 0.0 | 0.0 |
| 6-Bromo-2-(5-iso- | 1.000 | 4.0 | | 0.0 | 9.0 | 2.0 | 0.0 | 2.0 | 8.0 | 2.0 | | 9.0 | 9.0 | | 9.0 | 9.0 |

TABLE I-continued

POST-EMERGENCE TESTS - RATES IN KG/HA

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE, NATO | SOY-BEAN WI | SUN-FLR XXX | S WHEAT ER |
|---|---|---|---|---|---|---|---|---|---|---|---|---|---|---|---|---|
| propyl-5-methyl-4-oxo-2-imidazolin-2-yl)-3-quinoline carboxylic acid | .500 | 2.0 | | 0.0 | 8.0 | 1.0 | 0.0 | 2.0 | 2.0 | 0.0 | | 9.0 | 7.0 | 0.0 | 9.0 | 6.0 |
| | .250 | 2.0 | | 0.0 | 8.0 | 0.0 | 0.0 | 0.0 | 2.0 | 0.0 | | 8.0 | 5.0 | 0.0 | 9.0 | 5.0 |
| | .125 | 0.0 | | 0.0 | 6.0 | 0.0 | 0.0 | 0.0 | 0.0 | 0.0 | | 4.0 | 5.0 | 0.0 | 9.0 | 4.0 |
| | .063 | 0.0 | | 0.0 | 3.0 | 0.0 | 0.0 | 0.0 | 0.0 | 0.0 | | 3.0 | 3.0 | 0.0 | 9.0 | 4.0 |
| | .032 | 0.0 | | 0.0 | 3.0 | 0.0 | 0.0 | 0.0 | 0.0 | 0.0 | | 2.0 | 2.0 | 0.0 | 9.0 | 4.0 |
| Methyl 2-(5-isopropyl-5-methyl-4-oxo-2-imidazolin-2-yl)-8-nitro-3-quinolinecarboxylate | 8.000 | 9.0 | 5.0 | 0.0 | 9.0 | 0.0 | 5.0 | 0.0 | 0.0 | 0.0 | | | | | | |
| 2-(5-Ethyl-5-methyl-4-oxo-2-imidazolin-2-yl)-3-quinoline carboxylic acid | 1.000 | 9.0 | | 9.0 | 9.0 | 9.0 | 9.0 | 7.0 | 8.0 | 8.0 | | 9.0 | 9.0 | 4.0 | 9.0 | 7.0 |
| | .500 | 9.0 | | 9.0 | 9.0 | 9.0 | 6.0 | 7.0 | 7.0 | 5.0 | | 9.0 | 6.0 | 3.0 | 9.0 | 7.0 |
| | .250 | 7.0 | | 9.0 | 9.0 | 7.0 | 4.0 | 4.0 | 6.0 | 3.0 | | 9.0 | 5.0 | 3.0 | 9.0 | 4.0 |
| | .125 | 4.0 | | 7.0 | 8.0 | 7.0 | 4.0 | 4.0 | 3.0 | 1.0 | | 9.0 | 5.0 | 2.0 | 9.0 | 3.0 |
| | .063 | 2.0 | | 5.0 | 4.0 | 3.0 | 4.0 | 2.0 | 2.0 | 0.0 | | 9.0 | 3.0 | 0.0 | 9.0 | 3.0 |
| | .032 | 0.0 | | 3.0 | 1.0 | 2.0 | 0.0 | 1.0 | 2.0 | 0.0 | | 6.0 | 3.0 | 0.0 | 9.0 | 3.0 |
| | | | | | | | | | | | | | 9.0 | 7.0 | 0.0 | 4.0 | 2.0 |
| 8-Chloro-2-(5-isopropyl-5-methyl-4-oxo-2-imidazolin-2-yl)-3-quinoline carboxylic acid | 1.000 | 8.0 | | 3.0 | 6.0 | 7.0 | 4.0 | 5.0 | 9.0 | 7.0 | | 9.0 | 4.0 | 3.0 | 9.0 | 4.0 |
| | .500 | 2.0 | | 3.0 | 3.0 | 5.0 | 3.0 | 3.0 | 8.0 | 5.0 | | 9.0 | 3.0 | 2.0 | 9.0 | 1.0 |
| | .250 | 0.0 | | 1.0 | 1.0 | 2.0 | 0.0 | 1.0 | 8.0 | 4.0 | | 7.0 | 3.0 | 2.0 | 9.0 | 0.0 |
| | .125 | 0.0 | | 0.0 | 0.0 | 1.0 | 0.0 | 0.0 | 3.0 | 4.0 | | 7.0 | 3.0 | 0.0 | 8.0 | 0.0 |
| | .063 | 0.0 | | 0.0 | 0.0 | 0.0 | 0.0 | 0.0 | 2.0 | 2.0 | | 6.0 | 2.0 | 0.0 | 8.0 | 0.0 |
| | .032 | 0.0 | | 0.0 | 0.0 | 0.0 | 0.0 | 0.0 | 2.0 | 0.0 | | 6.0 | 2.0 | 0.0 | 8.0 | 0.0 |
| 6-Fluoro-2-(5-isopropyl-5-methyl-4-oxo-2-imidazolin-2-yl)-3-quinoline carboxylic acid | 1.000 | 9.0 | | 7.0 | 9.0 | 9.0 | 8.0 | 8.0 | 9.0 | 9.0 | | 9.0 | 6.0 | 5.0 | 9.0 | 9.0 |
| | .500 | 9.0 | | 6.0 | 9.0 | 8.0 | 8.0 | 7.0 | 8.0 | 9.0 | | 9.0 | 5.0 | 4.0 | 9.0 | 9.0 |
| | .250 | 8.0 | | 6.0 | 9.0 | 8.0 | 8.0 | 6.0 | 8.0 | 9.0 | | 9.0 | 5.0 | 3.0 | 9.0 | 9.0 |
| | .125 | 8.0 | | 3.0 | 9.0 | 7.0 | 6.0 | 3.0 | 6.0 | 8.0 | | 9.0 | 5.0 | 2.0 | 9.0 | 9.0 |
| | .063 | 8.0 | | 2.0 | 8.0 | 6.0 | 5.0 | 2.0 | 6.0 | 6.0 | | 8.0 | 4.0 | 1.0 | 9.0 | 8.0 |
| | .032 | 5.0 | | 1.0 | 0.0 | 4.0 | 2.0 | 1.0 | 2.0 | 5.0 | | 8.0 | 3.0 | 1.0 | 9.0 | 5.0 |
| 2-(5-Isopropyl-5-methyl-4-oxo-2-imidazolin-2-yl)-8-methoxy-3-quinolinecarboxylic acid | 1.000 | 9.0 | | 7.0 | 9.0 | 6.0 | 2.0 | 3.0 | 8.0 | 9.0 | | 9.0 | 6.0 | 6.0 | 9.0 | 9.0 |
| | .500 | 7.0 | | 4.0 | 9.0 | 5.0 | 1.0 | 1.0 | 8.0 | 9.0 | | 9.0 | 5.0 | 5.0 | 9.0 | 9.0 |
| | .250 | 5.0 | | 2.0 | 9.0 | 4.0 | 1.0 | 1.0 | 7.0 | 9.0 | | 9.0 | 5.0 | 5.0 | 9.0 | 9.0 |
| | .125 | 1.0 | | 0.0 | 8.0 | 3.0 | 1.0 | 0.0 | 6.0 | 0.0 | | 9.0 | 4.0 | 4.0 | 9.0 | 3.0 |
| | .063 | 0.0 | | 0.0 | 8.0 | 1.0 | 0.0 | 0.0 | 1.0 | 0.0 | | 9.0 | 3.0 | 3.0 | 8.0 | 3.0 |
| | .032 | 0.0 | | 0.0 | 7.0 | 0.0 | 0.0 | 0.0 | 0.0 | 0.0 | | 9.0 | 2.0 | 3.0 | 8.0 | 3.0 |

| Compound | RATE | BARN-YARD GR | GREEN FOX | P NUT-SEDGE | WILD OATS | QUACK GRASS | FLD BIND-WD | MRN-GLRY SP | RAG-WEED | VELVET-LEAF | S BARLY LA | CORN FIELD | RICE, NATO | SOY-BEAN WI | SUN-FLR XXX | S WHEAT ER |
|---|---|---|---|---|---|---|---|---|---|---|---|---|---|---|---|---|
| 2-(5-Isopropyl)-5-methyl-4-oxo-2-imidazolin-2-yl)-6-(trifluoromethyl)-3-quinolinecarboxylic acid | 1.000 | 8.0 | | 0.0 | 9.0 | 6.0 | 2.0 | 2.0 | 9.0 | 3.0 | | 8.0 | 5.0 | | 9.0 | 9.0 |
| | .500 | 6.0 | | 0.0 | 8.0 | 4.0 | 1.0 | 1.0 | 8.0 | 1.0 | | 7.0 | 5.0 | | 9.0 | 6.0 |
| | .250 | 2.0 | | 0.0 | 7.0 | 1.0 | 0.0 | 1.0 | | 0.0 | | 7.0 | 2.0 | | 9.0 | 6.0 |

EXAMPLE 11

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table II below. Where more than one test is involved for a given compound, the data are averaged.

TABLE II

PRE-EMERGENCE TESTS - RATES IN KG/HA

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN WI | SUN-FLR XXX | S WHEAT ER |
|---|---|---|---|---|---|---|---|---|---|---|---|---|---|---|---|---|---|
| 2-(5-Isopropyl-5-methyl-4-oxo-2-imidazolin-2-yl)-3-quinolinecarboxylic acid | 8.000 | 9.0 | 9.0 | 9.0 | 9.0 | 9.0 | 9.0 | 8.0 | 9.0 | 8.0 | | | | | | 9.0 | 9.0 |
| | 4.000 | 9.0 | 9.0 | 9.0 | 9.0 | 9.0 | 9.0 | 9.0 | 9.0 | 9.0 | 9.0 | 9.0 | | 9.0 | | 9.0 | 9.0 |
| | 1.000 | 8.8 | 9.0 | 9.0 | 8.9 | 9.0 | 9.0 | 8.5 | 9.0 | 8.8 | 9.0 | 9.0 | | 9.0 | | 8.7 | 8.9 |
| | .500 | 8.3 | 8.8 | 9.0 | 8.6 | 9.0 | 9.0 | 8.0 | 8.9 | 8.5 | 9.0 | 8.8 | | 9.0 | 6.5 | 8.6 | 8.6 |
| | .250 | | | | | | | | 7.9 | 8.0 | | | | | 4.0 | | |
| 2-(5-Isopropyl-5-methyl-4-oxo-2-imidazolin-2-yl)-6-nitro-3-quinolinecarboxylic acid | 4.000 | 9.0 | 9.0 | 8.0 | 9.0 | 9.0 | 9.0 | 9.0 | 8.0 | 9.0 | | 9.0 | | 9.0 | 3.6 | 9.0 | 9.0 |
| | 1.000 | 9.0 | 8.0 | 7.0 | 7.0 | 9.0 | 9.0 | 8.5 | 8.0 | 7.0 | | 8.5 | | 9.0 | | 8.0 | 8.5 |
| | .500 | 8.5 | | 7.0 | 7.0 | 9.0 | 9.0 | 8.5 | 7.5 | 6.0 | | 9.0 | | 9.0 | | 8.0 | 7.0 |
| | .250 | 9.0 | | 3.0 | 8.0 | 9.0 | 9.0 | 8.0 | 9.0 | 4.0 | | | | | | | |
| 6-(Difluoromethoxy)-2-(5-isopropyl-5-methyl-4-oxo-2-imidazolin-2-yl)-3-quinolinecarboxylic acid | .500 | 9.0 | | 2.0 | 9.0 | 9.0 | 9.0 | 9.0 | 9.0 | 8.0 | | 9.0 | | 9.0 | | 9.0 | 9.0 |
| | .250 | 5.0 | | 1.0 | 9.0 | 9.0 | 9.0 | 9.0 | 9.0 | 7.0 | | 9.0 | | 8.0 | | 9.0 | 8.0 |
| | .125 | 4.0 | | 0.0 | 9.0 | 9.0 | 7.0 | 8.0 | 9.0 | 5.0 | | 9.0 | | 8.0 | | 9.0 | 8.0 |
| | .063 | 0.0 | | 0.0 | 6.0 | 7.0 | 2.0 | 6.0 | 9.0 | 3.0 | | 9.0 | | 6.0 | | 9.0 | 7.0 |
| 2-(5-Isopropyl-5-methyl-4-oxo-2-imidazolin-2-yl)-8-methoxy-3-quinolinecarboxylic acid | .500 | 7.0 | | 9.0 | 9.0 | 9.0 | 9.0 | 7.0 | 7.0 | 7.0 | | 9.0 | | 9.0 | | 9.0 | 8.0 |
| | .250 | 7.0 | | 8.0 | 9.0 | 9.0 | 9.0 | 6.0 | 7.0 | 6.0 | | 9.0 | | 9.0 | | 9.0 | 7.0 |
| | .125 | 3.0 | | 7.0 | 9.0 | 9.0 | 6.0 | 3.0 | 1.0 | 2.0 | | 9.0 | | 8.0 | | 9.0 | 7.0 |
| | .063 | 2.0 | | 7.0 | 3.0 | 7.0 | 4.0 | 1.0 | 0.0 | 2.0 | | 9.0 | | 8.0 | | 8.0 | 3.0 |
| 2-(5-Isopropyl-5-methyl-4-thiono-2-imidazolin-2-yl)-nicotinic acid | .500 | 9.0 | 9.0 | 9.0 | 9.0 | 9.0 | 9.0 | 9.0 | 9.0 | 9.0 | | 9.0 | | 9.0 | | 9.0 | 9.0 |
| | .250 | 8.0 | 9.0 | 9.0 | 9.0 | 9.0 | 9.0 | 9.0 | 7.0 | 9.0 | | 9.0 | | 9.0 | | 9.0 | 9.0 |
| | .125 | 7.0 | 9.0 | 9.0 | 9.0 | 9.0 | 9.0 | 9.0 | 4.0 | 9.0 | | 9.0 | | 9.0 | | 9.0 | 9.0 |
| | .063 | 5.0 | 4.0 | 7.0 | 9.0 | 9.0 | 8.0 | 4.0 | 4.0 | 3.0 | | 9.0 | | 6.0 | | 5.0 | 9.0 |
| | .032 | 1.0 | | 7.0 | 9.0 | 7.0 | 2.0 | 1.0 | 0.0 | 0.0 | | 9.0 | | 6.0 | | 5.0 | 9.0 |
| Sodium 2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 9.0 | 9.0 | 9.0 | | 9.0 | | 9.0 | | 9.0 | 9.0 |
| | 1.000 | 9.0 | 9.0 | 9.0 | 9.0 | 9.0 | 9.0 | 9.0 | 9.0 | 9.0 | | 9.0 | | 9.0 | | 9.0 | 9.0 |
| | .660 | 9.0 | | 9.0 | 9.0 | 9.0 | 9.0 | 9.0 | 9.0 | 9.0 | | 9.0 | | 9.0 | | 9.0 | 9.0 |
| | .500 | 9.0 | | 9.0 | 9.0 | 9.0 | 9.0 | 9.0 | 9.0 | 8.0 | | 9.0 | | 9.0 | | 9.0 | 9.0 |
| | .330 | 9.0 | 9.0 | 9.0 | 9.0 | 9.0 | 9.0 | 9.0 | 9.0 | 9.0 | | 9.0 | | 9.0 | | 9.0 | 9.0 |
| 2-(5-Isopropyl-5-methyl-4-oxo-2-imidazolin-2-yl)-3-quinolinecarboxaldehyde | 4.000 | 9.0 | 9.0 | 9.0 | 9.0 | 9.0 | 9.0 | 9.0 | 9.0 | 9.0 | | 9.0 | | 9.0 | | 9.0 | 9.0 |
| | 1.000 | 9.0 | | 9.0 | 9.0 | 9.0 | 9.0 | 9.0 | 9.0 | 9.0 | | 9.0 | | 9.0 | | 9.0 | 9.0 |
| 2-[3-(Hydroxymethyl)-2-quinolyl]-5-isopropyl-5-methyl-2-imidazolin-4-one | 4.000 | 9.0 | | 9.0 | 9.0 | 9.0 | 9.0 | 9.0 | 9.0 | 9.0 | | 9.0 | | 9.0 | | 9.0 | 9.0 |
| | .500 | 9.0 | | 9.0 | 9.0 | 9.0 | 9.0 | 9.0 | 9.0 | 8.0 | | 9.0 | | 9.0 | | 9.0 | 8.0 |
| | .250 | 8.0 | | 9.0 | 9.0 | 9.0 | 9.0 | 9.0 | 9.0 | 7.0 | | 9.0 | | 9.0 | | 9.0 | 7.0 |
| | .125 | 7.0 | | 9.0 | 8.0 | 9.0 | 9.0 | 9.0 | 9.0 | 7.0 | | 9.0 | | 9.0 | | 7.0 | 7.0 |
| | .063 | 5.0 | | 9.0 | 7.0 | 9.0 | 9.0 | 8.0 | 9.0 | 6.0 | | 9.0 | | 6.0 | | 7.0 | 6.0 |

| Compound | RATE | BARN-YARD GR | GREEN FOX | NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN AD | SUN-FLR XXX | S WHEAT ER |

TABLE II-continued

PRE-EMERGENCE TESTS - RATES IN KG/HA

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | CORN FIELD | COT-TON | RICE, NATO | SOY-BEAN WI | SUN-FLR XXX | S WHEAT ER |
|---|---|---|---|---|---|---|---|---|---|---|---|---|---|---|---|---|
| Methyl 2-(1-acetyl-4-isopropyl-4-methyl-5-oxo-2-imidazolin-2-yl)-3-quinolinecarboxylate | .500 | 9.0 | 9.0 | 8.0 | 8.0 | 8.0 | 9.0 | 3.0 | 7.0 | 6.0 | 9.0 | | 9.0 | 6.0 | 9.0 | 8.0 |
| | .250 | 8.0 | 9.0 | 8.0 | 8.0 | 9.0 | 9.0 | 3.0 | 8.0 | 3.0 | 9.0 | | 7.0 | 3.0 | 9.0 | 7.0 |
| | .125 | 7.0 | | 8.0 | 7.0 | 9.0 | 9.0 | 0.0 | 3.0 | 1.0 | 6.0 | | 7.0 | 1.0 | 7.0 | 7.0 |
| | .063 | 1.0 | | 8.0 | 4.0 | 7.0 | 9.0 | 0.0 | 1.0 | 0.0 | 1.0 | | 4.0 | 0.0 | 7.0 | 7.0 |
| | .032 | 1.0 | | 8.0 | 1.0 | 3.0 | 7.0 | 0.0 | 1.0 | 0.0 | 0.0 | | 0.0 | 0.0 | 1.0 | 2.0 |
| 2-(5-Isopropyl-5-methyl-4-oxo-2-imidazolin-2-yl)-6-(trifluoromethyl)-3-quinolinecarboxylic acid | .500 | 7.0 | | 0.0 | 9.0 | 9.0 | 9.0 | 0.0 | 9.0 | 5.0 | 8.0 | | 0.0 | 6.0 | 9.0 | 8.0 |
| | .250 | 5.0 | | 0.0 | 8.0 | 4.0 | 9.0 | 8.0 | 8.0 | 2.0 | 2.0 | | 7.0 | 2.0 | 9.0 | 7.0 |
| | .125 | 1.0 | | 0.0 | 8.0 | 1.0 | 0.0 | 0.0 | 8.0 | 2.0 | 2.0 | | 5.0 | 2.0 | 8.0 | 5.0 |
| | .063 | 0.0 | | 0.0 | 3.0 | 0.0 | 0.0 | 0.0 | 4.0 | 0.0 | 1.0 | | 2.0 | 1.0 | 7.0 | 2.0 |
| | .032 | 0.0 | | 0.0 | 2.0 | 0.0 | 0.0 | 0.0 | 0.0 | 0.0 | 1.0 | | 0.0 | 0.0 | 7.0 | 1.0 |
| Methyl 2-(5-Iso-propyl-5-methyl-4-oxo-2-imidazolin-2-yl)-6-nitro-3-quinolinecarboxylate | .500 | 0.0 | | 0.0 | 0.0 | 0.0 | 8.0 | 0.0 | 0.0 | 0.0 | 0.0 | | 0.0 | 0.0 | 0.0 | 0.0 |
| 6,7-Dichloro-2-(5-isopropyl-5-methyl-4-oxo-2-imidazolin-2-yl)-3-quinolinecarboxylate | .500 | 8.0 | | 9.0 | 8.0 | 9.0 | 9.0 | 8.0 | 9.0 | 4.0 | 5.0 | | 8.0 | 4.0 | 8.0 | 7.0 |
| | .250 | 0.0 | | 2.0 | 8.0 | 7.0 | 3.0 | 6.0 | 2.0 | 2.0 | 3.0 | | 7.0 | 1.0 | 8.0 | 6.0 |
| | .125 | 0.0 | | | 5.0 | 7.0 | 3.0 | 0.0 | 2.0 | 2.0 | 3.0 | | 2.0 | 1.0 | 7.0 | 4.0 |
| | .063 | 0.0 | | 2.0 | 0.0 | 2.0 | 0.0 | 0.0 | 1.0 | 1.0 | 0.0 | | 0.0 | 0.0 | 7.0 | 3.0 |
| | .032 | 0.0 | | | 0.0 | 0.0 | 0.0 | 0.0 | 0.0 | 1.0 | 0.0 | | 0.0 | 0.0 | 3.0 | 2.0 |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN AD | SUN-FLR XXX | S WHEAT ER |
|---|---|---|---|---|---|---|---|---|---|---|---|---|---|---|---|---|---|
| Diisopropylammonium 2-(5-isopropyl-5-methyl-4-oxo-2-imidazolin-2-yl)-3-quinolinecarboxylate | 4.000 | 9.0 | | 9.0 | 9.0 | 9.0 | 9.0 | 9.0 | 9.0 | 9.0 | | 9.0 | | 9.0 | | 9.0 | |
| | 1.000 | 9.0 | | 9.0 | 9.0 | 9.0 | 9.0 | 9.0 | 9.0 | 9.0 | | 9.0 | | 9.0 | | 9.0 | |
| | .750 | 9.0 | | 9.0 | 9.0 | 9.0 | 9.0 | 8.0 | 9.0 | 9.0 | | 9.0 | | 9.0 | | 9.0 | |
| | .500 | 9.0 | | 9.0 | 9.0 | 9.0 | 9.0 | 9.0 | 9.0 | 9.0 | | 9.0 | | 9.0 | | 9.0 | |
| | .375 | 9.0 | | 9.0 | 9.0 | 9.0 | 9.0 | 9.0 | 9.0 | 9.0 | | 9.0 | | 9.0 | | 9.0 | |
| | .250 | 9.0 | | 9.0 | 9.0 | 9.0 | 9.0 | 9.0 | 9.0 | 9.0 | | 9.0 | | 9.0 | | 9.0 | |
| Calcium 2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 9.0 | 9.0 | 9.0 | | 9.0 | | 9.0 | | 9.0 | |
| | 1.000 | 9.0 | 9.0 | 9.0 | 9.0 | 9.0 | 9.0 | 9.0 | 9.0 | 9.0 | | 9.0 | | 9.0 | | 9.0 | |
| | .500 | 9.0 | | 9.0 | 9.0 | 9.0 | 9.0 | 9.0 | 9.0 | 9.0 | | 9.0 | | 9.0 | | 9.0 | |
| | .250 | 9.0 | | 9.0 | 9.0 | 9.0 | 9.0 | 9.0 | 9.0 | 9.0 | | 9.0 | | 9.0 | | 9.0 | |
| | .125 | 9.0 | 9.0 | 9.0 | 9.0 | 9.0 | 9.0 | 9.0 | 9.0 | 9.0 | | 9.0 | | 9.0 | | 9.0 | |
| 6-Chloro-2-(5-isopropyl-5-methyl-4-oxo-2-imidazolin-2-yl)-3-quinolinecarboxylate | 4.000 | 9.0 | | 8.0 | 9.0 | 9.0 | 8.0 | 9.0 | 9.0 | 8.0 | | 8.5 | | 9.0 | 5.0 | 9.0 | |
| | 2.000 | 9.0 | | 9.0 | 9.0 | 9.0 | 7.5 | 9.0 | 9.0 | 8.0 | | 8.0 | | 9.0 | 2.0 | 9.0 | |
| | 1.000 | 9.0 | 9.0 | 7.8 | 8.5 | 9.0 | 7.5 | 7.5 | 8.5 | 7.0 | | 3.7 | | 8.5 | 0.5 | 8.5 | |
| | .500 | 8.0 | | 6.3 | 8.5 | 9.0 | 7.5 | 7.5 | 8.5 | 7.0 | | 3.7 | | 8.5 | 0.5 | 8.5 | |
| | .250 | 8.0 | 9.0 | 6.3 | 9.0 | 9.0 | 9.0 | 9.0 | 9.0 | 7.0 | | | | | | 9.0 | |
| | .125 | 8.0 | | 8.0 | 9.0 | 9.0 | 9.0 | 9.0 | 9.0 | 9.0 | | 9.0 | | | | 9.0 | |
| 2-(5-isopropyl-5-methyl-4-oxo-2-imidazolin-2-yl)-7-methyl-3-quinolinecarboxylic acid | 4.000 | 9.0 | 9.0 | 8.0 | 9.0 | 9.0 | 9.0 | 9.0 | 9.0 | 9.0 | | 9.0 | | | | 9.0 | |
| | 1.000 | 9.0 | 9.0 | 9.0 | 9.0 | 9.0 | 9.0 | 9.0 | 7.0 | 8.0 | | 9.0 | | | | 8.0 | |
| | .500 | 9.0 | | 9.0 | 5.0 | 9.0 | | | | | | | | | | | |

4,843,162

TABLE II-continued
PRE-EMERGENCE TESTS - RATES IN KG/HA

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN BR | SUN-FLR XXX | S WHEAT ER |
|---|---|---|---|---|---|---|---|---|---|---|---|---|---|---|---|---|---|
| Ethylammonium 2-(5-isopropyl-4-oxo-2-imidazolin-2-yl)-3-quinoline-carboxylate | .645 | 9.0 | | 9.0 | 9.0 | 9.0 | 9.0 | 7.0 | 9.0 | 9.0 | | 9.0 | | 9.0 | 5.0 | 9.0 | 9.0 |
| | .323 | 9.0 | | 9.0 | 8.0 | 9.0 | 9.0 | 8.0 | 9.0 | 9.0 | | 9.0 | | 9.0 | 4.0 | 9.0 | 9.0 |
| | .161 | 6.0 | | 9.0 | 8.0 | 9.0 | 9.0 | 8.0 | 9.0 | 8.0 | | 9.0 | | 9.0 | 4.0 | 9.0 | 9.0 |
| | .031 | 7.0 | | 9.0 | 8.0 | 7.0 | 9.0 | 7.0 | 8.0 | 8.0 | | 9.0 | | 9.0 | 2.0 | 7.0 | 6.0 |
| | .040 | 3.0 | | 8.0 | 7.0 | 6.0 | 9.0 | 7.0 | 8.0 | 7.0 | | 9.0 | | 9.0 | 2.0 | 7.0 | 3.0 |
| Methylammonium 2-(5-isopropyl-5-methyl-4-oxo-2-imidazolin-2-yl)-3-quinoline-carboxylate | .610 | 9.0 | | 9.0 | 9.0 | 9.0 | 9.0 | 8.0 | 9.0 | 9.0 | | 9.0 | | 9.0 | 7.0 | 9.0 | 9.0 |
| | .305 | 9.0 | | 9.0 | 9.0 | 9.0 | 9.0 | 7.0 | 9.0 | 9.0 | | 9.0 | | 9.0 | 5.0 | 9.0 | 9.0 |
| | .153 | 9.0 | | 9.0 | 8.0 | 9.0 | 9.0 | 7.0 | 9.0 | 9.0 | | 9.0 | | 9.0 | 4.0 | 7.0 | 7.0 |
| | .076 | 8.0 | | 9.0 | 8.0 | 9.0 | 9.0 | 8.0 | 9.0 | 8.0 | | 9.0 | | 9.0 | 3.0 | 7.0 | 5.0 |
| Dimethylammonium 2-(5-isopropyl-5-methyl-4-oxo-2-imidazolin-2-yl)-3-quinoline-carboxylate | .650 | 9.0 | | 9.0 | 9.0 | 9.0 | 9.0 | 8.0 | 9.0 | 9.0 | | 9.0 | | 9.0 | 3.0 | 9.0 | 9.0 |
| | .325 | 9.0 | | 9.0 | 8.0 | 9.0 | 9.0 | 8.0 | 9.0 | 8.0 | | 9.0 | | 9.0 | 4.0 | 9.0 | 9.0 |
| | .163 | 4.0 | | 9.0 | 8.0 | 9.0 | 9.0 | 6.0 | 8.0 | 9.0 | | 9.0 | | 9.0 | 4.0 | 8.0 | 9.0 |
| | .081 | | | 9.0 | 8.0 | 9.0 | 9.0 | 8.0 | 8.0 | 8.0 | 9.0 | 9.0 | 2.0 | 8.0 | 7.0 | | |
| Butyl 2-(5-isopropyl-5-methyl-4-oxo-2-imidazolin-2-yl)-3-quinolinecarboxylate | 4.000 | 9.0 | 9.0 | 8.0 | 9.0 | 9.0 | 9.0 | 8.0 | 9.0 | 9.0 | | 9.0 | | 9.0 | 9.0 | 9.0 | 9.0 |
| | 1.000 | 7.0 | 9.0 | 8.0 | 4.0 | 9.0 | 9.0 | 3.0 | 6.0 | 8.0 | | 8.0 | | 2.0 | 3.0 | 7.0 | 3.0 |
| | .500 | 2.0 | 4.0 | 7.0 | 2.0 | 3.0 | 8.0 | 1.0 | 0.0 | 4.0 | | 3.0 | | 1.0 | 2.0 | 3.0 | 3.0 |
| | .250 | 1.0 | 1.0 | 1.0 | 1.0 | 9.0 | 9.0 | 0.0 | 0.0 | 3.0 | | 2.0 | | 0.0 | 1.0 | 2.0 | 0.0 |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN BR | SUN-FLR XXX | S WHEAT ER |
|---|---|---|---|---|---|---|---|---|---|---|---|---|---|---|---|---|---|
| 8-Chloro-2-(5-isopropyl-5-methyl-4-oxo-2-imidazolin-2-yl)-3-quinoline-carboxylic acid | 5.000 | 9.0 | | 9.0 | 9.0 | 9.0 | 9.0 | 9.0 | 9.0 | 9.0 | | 9.0 | 7.0 | 9.0 | 1.0 | 9.0 | |
| | .500 | 3.0 | | 4.0 | 6.0 | 9.0 | 9.0 | 7.0 | 9.0 | 6.0 | | 8.0 | 7.0 | 9.0 | 1.0 | 9.0 | |
| | .250 | 1.0 | 0.0 | 3.0 | 4.0 | 7.0 | 9.0 | 5.0 | 9.0 | 5.0 | | 8.0 | 4.0 | 8.0 | 0.0 | 7.0 | |
| | .125 | 1.0 | | 3.0 | | 4.0 | 6.0 | 3.0 | 6.0 | 3.0 | | 3.0 | 3.0 | 7.0 | 0.0 | 7.0 | |
| | .063 | 0.0 | | 0.0 | 1.0 | 0.0 | | 3.0 | 9.0 | 1.0 | | 3.0 | 2.0 | 7.0 | 0.0 | 5.0 | |
| | .032 | 0.0 | | 0.0 | 1.0 | 0.0 | | 2.0 | 6.0 | 1.0 | | 1.0 | 1.0 | 4.0 | 0.0 | 5.0 | |
| | .016 | 0.0 | | 0.0 | 0.0 | 0.0 | 1.0 | 0.0 | 0.0 | 0.0 | | 1.0 | 0.0 | 2.0 | 0.0 | 3.0 | |
| Methyl 6-(dimethyl-amino)-2-(5-iso-propyl-5-methyl-4-oxo-2-imidazolin-2-yl)-3-quinoline-carboxylate | .250 | 0.0 | | 8.0 | 0.0 | 0.0 | 0.0 | 0.0 | 0.0 | 0.0 | 0.0 | 1.0 | 0.0 | 0.0 | 0.0 | | |
| | .125 | 0.0 | | 0.0 | 0.0 | 0.0 | 0.0 | 0.0 | 0.0 | 0.0 | 0.0 | 0.0 | 0.0 | 0.0 | 0.0 | | |
| | .063 | 0.0 | | 8.0 | 0.0 | 0.0 | 0.0 | 0.0 | 0.0 | 0.0 | 0.0 | 0.0 | 0.0 | 0.0 | 0.0 | | |
| | .032 | 0.0 | | 8.0 | 0.0 | 0.0 | 0.0 | 0.0 | 0.0 | 0.0 | 0.0 | 0.0 | 0.0 | 0.0 | 0.0 | | |
| Isopropylammonium 2-(5-isopropyl-5-methyl-4-oxo-2-imidazolin-2-yl)-3-quinolinecarbo-xylate | .660 | 9.0 | | 9.0 | 9.0 | 9.0 | 9.0 | 7.0 | 9.0 | 9.0 | 9.0 | 9.0 | 6.0 | 9.0 | 1.0 | 9.0 | |
| | .330 | 8.0 | | 9.0 | 8.0 | 9.0 | 8.0 | 8.0 | 9.0 | 6.0 | 9.0 | 8.0 | 6.0 | 9.0 | 1.0 | 9.0 | |
| | .165 | 8.0 | | 9.0 | 8.0 | 9.0 | 9.0 | 7.0 | 9.0 | 5.0 | 9.0 | 8.0 | 1.0 | 8.0 | 0.0 | 7.0 | |
| | .083 | 8.0 | | 9.0 | 8.0 | 9.0 | 8.0 | 8.0 | 9.0 | 3.0 | 9.0 | 9.0 | 4.0 | 7.0 | 0.0 | 5.0 | |
| | .041 | 3.0 | | 9.0 | 5.0 | 9.0 | 6.0 | 6.0 | 9.0 | 7.0 | 9.0 | 9.0 | 3.0 | 7.0 | 0.0 | 3.0 | |
| Octylammonium 2-(5-isopropyl-5-methyl-4-oxo-2-imidazolin-2-yl)-3-quinoline-carboxylate | .785 | 9.0 | | 9.0 | 9.0 | 9.0 | 9.0 | 8.0 | 9.0 | 9.0 | 9.0 | 9.0 | 2.0 | 9.0 | 9.0 | 9.0 | |
| | .393 | 9.0 | | 9.0 | 9.0 | 9.0 | 9.0 | 8.0 | 9.0 | 9.0 | 9.0 | 9.0 | 3.0 | 9.0 | 9.0 | 9.0 | |
| | .196 | 9.0 | | 9.0 | 8.0 | 9.0 | 9.0 | 7.0 | 9.0 | 8.0 | 9.0 | 9.0 | 2.0 | 8.0 | 9.0 | 9.0 | |
| | .198 | 8.0 | | 9.0 | 8.0 | 9.0 | 9.0 | 7.0 | 9.0 | 8.0 | 9.0 | 9.0 | 4.0 | 8.0 | 6.0 | 9.0 | |
| | .047 | 2.0 | | 8.0 | 7.0 | 9.0 | 9.0 | 7.0 | 9.0 | 7.0 | 9.0 | 9.0 | 0.0 | 8.0 | 5.0 | 9.0 | |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN AD | SUN-FLR XXX | S WHEAT ER |
|---|---|---|---|---|---|---|---|---|---|---|---|---|---|---|---|---|---|
| 2-(5-Isopropyl-5- | 4.000 | 9.0 | 9.0 | 8.0 | 9.0 | 9.0 | 9.0 | 9.0 | 8.0 | 9.0 | | 9.0 | | 9.0 | 3.0 | 9.0 | 9.0 |

TABLE II-continued
PRE-EMERGENCE TESTS - RATES IN KG/HA

| Compound | Rate | | | | | | | | | | | | | |
|---|---|---|---|---|---|---|---|---|---|---|---|---|---|---|
| methyl-4-oxo-2-imidazolin-2-yl)-6-nitro-3-quinoline-carboxylic acid | 1.000 | 9.0 | 9.0 | 9.0 | 9.0 | 9.0 | 9.0 | 8.0 | 9.0 | 7.0 | | 9.0 | 8.0 | 9.0 |
| | .500 | 8.5 | 8.0 | 7.0 | 9.0 | 8.5 | 7.5 | 8.5 | 8.5 | 6.0 | | 9.0 | 8.0 | 8.5 |
| | .250 | 9.0 | 3.0 | 8.0 | 9.0 | 8.0 | 9.0 | 9.0 | 9.0 | 4.0 | | 9.0 | 8.0 | 7.0 |
| | .125 | 6.0 | 3.0 | 3.0 | 8.0 | 5.0 | 9.0 | 2.0 | 9.0 | 4.0 | | 7.0 | 7.0 | 5.0 |
| | .063 | 2.0 | 1.0 | 1.0 | 9.0 | 5.0 | 2.0 | 8.0 | 7.0 | 2.0 | | 7.0 | 5.0 | 3.0 |
| 2-(5-Isopropyl-5-methyl-4-oxo-2-imidazolin-2-yl)-6-methyl-3-quinolinecarboxylic acid | .500 | 6.0 | 3.0 | 6.0 | 8.0 | 7.0 | 8.0 | 9.0 | 8.0 | 7.0 | | 9.0 | 7.0 | 9.0 |
| | .250 | 3.0 | 3.0 | 6.0 | 4.0 | 6.0 | 8.0 | 9.0 | 7.0 | 4.0 | | 9.0 | 7.0 | 9.0 |
| | .125 | 2.0 | 1.0 | 3.0 | 2.0 | 3.0 | 6.0 | 6.0 | 7.0 | 2.0 | | 8.0 | 7.0 | 9.0 |
| | .063 | 1.0 | 0.0 | 1.0 | 0.0 | 2.0 | 5.0 | 5.0 | 4.0 | 2.0 | | 6.0 | 4.0 | 6.0 |
| Methyl 2-(5-isopropyl-5-methyl-4-oxo-2-imidazolin-2-yl)-3-quinoline-carboxylate | .500 | 9.0 | | 2.0 | 4.0 | 2.0 | 9.0 | 3.0 | 3.0 | 2.0 | | 0.0 | 0.0 |
| | .250 | 9.0 | | 0.0 | 1.0 | 0.0 | 8.0 | 1.0 | 1.0 | 1.0 | | 0.0 | 0.0 |
| | .125 | 8.0 | | 0.0 | 0.0 | 0.0 | 8.0 | 0.0 | 0.0 | 0.0 | | 0.0 | 0.0 |
| 6-Bromo-2-(5-isopropyl-5-methyl-4-oxo-2-imidazolin-2-yl)-3-quinoline-carboxylic acid | .500 | 8.0 | | 2.0 | 7.0 | 7.0 | 8.0 | 7.0 | 5.0 | | 7.0 | 4.0 | 9.0 | 8.0 |
| | .250 | 6.0 | | 1.0 | 7.0 | 6.0 | 8.0 | 6.0 | 4.0 | | 4.0 | 2.0 | 9.0 | 8.0 |
| | .125 | 6.0 | | 0.0 | 7.0 | 4.0 | 7.0 | 4.0 | 4.0 | 4.0 | 7.0 | 6.0 | 9.0 | |
| | .063 | 3.0 | | 0.0 | 5.0 | 3.0 | 6.0 | 4.0 | 0.0 | 3.0 | 6.0 | 5.0 | 9.0 | |
| | .032 | 1.0 | | 0.0 | 5.0 | 3.0 | 6.0 | 3.0 | 0.0 | 2.0 | 4.0 | 4.0 | 9.0 | |
| Ammonium 2-(5-isopropyl-5-methyl-4-oxo-2-imidazolin-2-yl)-3-quinoline-carboxylate | 4.000 | 9.0 | 9.0 | 9.0 | 9.0 | 9.0 | 9.0 | 9.0 | 9.0 | 9.0 | | 9.0 | 9.0 | 9.0 |
| | 1.000 | 9.0 | 9.0 | 9.0 | 9.0 | 9.0 | 9.0 | 9.0 | 9.0 | 9.0 | | 9.0 | 9.0 | 9.0 |
| | .615 | 9.0 | | 9.0 | 9.0 | 9.0 | 9.0 | 9.0 | 9.0 | 9.0 | | 9.0 | 9.0 | 9.0 |
| | .500 | 9.0 | | 9.0 | 9.0 | 9.0 | 9.0 | 9.0 | 9.0 | 9.0 | 5.0 | 9.0 | 9.0 | 9.0 |
| | .308 | 9.0 | | 9.0 | 9.0 | 9.0 | 9.0 | 9.0 | 9.0 | 8.0 | 4.0 | 9.0 | 8.0 | 8.0 |
| Ethyl 2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 9.0 | 9.0 | 9.0 | | 9.0 | 9.0 | 9.0 |
| | 1.000 | 9.0 | 9.0 | 7.0 | 9.0 | 9.0 | 8.0 | 9.0 | 7.0 | 8.0 | 3.0 | 7.0 | 8.0 | 8.0 |
| | .500 | 8.0 | 4.0 | 5.0 | 8.0 | 8.0 | 3.0 | 7.0 | 4.0 | 7.0 | | 3.0 | 4.0 | 4.0 |
| 7-Chloro-2-(5-isopropyl-5-methyl-4-oxo-2-imidazolin-2-yl)-3-quinoline-carboxylic acid | 4.000 | 9.0 | 9.0 | 9.0 | 9.0 | 9.0 | 8.0 | 8.0 | 9.0 | 8.0 | | 9.0 | 9.0 | 7.0 |
| | 1.000 | 4.0 | 7.0 | 7.0 | 8.0 | 9.0 | 8.0 | 7.0 | 9.0 | 7.0 | | 9.0 | 7.0 | 5.0 |
| | .500 | 2.0 | 6.0 | 9.0 | 6.0 | 6.0 | 9.0 | 2.0 | 9.0 | 3.0 | | 9.0 | 7.0 | 3.0 |
| | .250 | 1.0 | 3.0 | 2.0 | 8.0 | 2.0 | 9.0 | 0.0 | 9.0 | 1.0 | | 3.0 | 5.0 | 2.0 |
| 2-(5-Isopropyl-5-methyl-4-oxo-2-imidazolin-2-yl)-7-methyl-3-quinolinecarboxylic acid | 4.000 | 9.0 | 9.0 | 8.0 | 9.0 | 9.0 | 9.0 | 9.0 | 9.0 | 8.0 | | 9.0 | 9.0 | 9.0 |
| | 1.000 | 9.0 | 9.0 | 8.0 | 9.0 | 9.0 | 9.0 | 9.0 | 9.0 | 8.0 | | 9.0 | 9.0 | 9.0 |
| | .500 | 9.0 | 9.0 | 9.0 | 9.0 | 5.0 | 9.0 | 7.0 | 9.0 | 8.0 | | 9.0 | 9.0 | 8.0 |
| 2-(5-Isopropyl-5-methyl-4-oxo-2-imidazolin-2-yl)-6-methoxy-3-quinolinecarboxylic acid | 8.000 | 9.0 | 9.0 | 9.0 | 9.0 | 8.0 | 8.0 | 8.0 | 9.0 | 8.0 | | 9.0 | 6.0 | 6.0 |
| | .500 | 9.0 | | 9.0 | 8.0 | 8.0 | 8.0 | 7.0 | | 8.0 | | 7.0 | 4.0 | 4.0 |
| | .250 | 7.0 | | 7.0 | 7.0 | 6.0 | 7.0 | 3.0 | | 7.0 | | 7.0 | 3.0 | 4.0 |
| | .125 | 5.0 | | 6.0 | 6.0 | 4.0 | 5.0 | 2.0 | | 6.0 | | 5.0 | 3.0 | 4.0 |
| | .063 | 4.0 | | 4.0 | 3.0 | 3.0 | 4.0 | 0.0 | | 6.0 | | 4.0 | 2.0 | 4.0 |
| 2-(5-Isopropyl-5-methyl-4-oxo-2-imidazolin-2-yl)-8-methoxy-7-nitro-3-quinolinecarboxylic acid | .500 | 2.0 | | 0.0 | 9.0 | 0.0 | 0.0 | 0.0 | 0.0 | 0.0 | | 9.0 | 2.0 | 1.0 |
| | .250 | 1.0 | | 0.0 | 7.0 | 0.0 | 0.0 | 0.0 | 0.0 | 0.0 | 3.0 | | 1.0 | 0.0 |

TABLE II-continued
PRE-EMERGENCE TESTS - RATES IN KG/HA

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN BR | SUN-FLR XXX | S WHEAT ER |
|---|---|---|---|---|---|---|---|---|---|---|---|---|---|---|---|---|---|
| 2-(5-Isopropyl-5-methyl-4-oxo-2-imidazolin-2-yl)-5-methyl-3-quinolinecarboxylic acid | .500 | 9.0 | | 3.0 | 8.0 | 9.0 | 9.0 | 7.0 | 9.0 | 6.0 | 9.0 | 9.0 | 6.0 | 5.0 | | | 7.0 |
| | .250 | 7.0 | | 2.0 | 9.0 | 9.0 | 9.0 | 7.0 | 8.0 | 5.0 | 9.0 | 9.0 | 5.0 | 5.0 | | | 6.0 |
| | .125 | 7.0 | | 1.0 | 7.0 | 6.0 | 9.0 | 6.0 | 6.0 | 3.0 | 9.0 | 9.0 | 4.0 | 5.0 | | | 5.0 |
| | .063 | 5.0 | | 1.0 | 5.0 | 4.0 | 9.0 | 3.0 | 4.0 | 1.0 | 8.0 | 8.0 | 4.0 | 4.0 | | | 3.0 |
| | .032 | 4.0 | | 0.0 | 4.0 | 4.0 | 0.0 | 2.0 | 4.0 | 1.0 | 6.0 | 6.0 | 3.0 | 3.0 | | | 2.0 |
| Tallowammonium 2-(5-isopropyl-5-methyl-4-oxo-2-imidazolin-2-yl)-3-quinolinecarboxylate | 1.040 | 9.0 | | 9.0 | 9.0 | 9.0 | 9.0 | 8.0 | 9.0 | 9.0 | 9.0 | 9.0 | | 8.0 | | | |
| | .520 | 9.0 | | 9.0 | 9.0 | 9.0 | 9.0 | 8.0 | 8.0 | 6.0 | 9.0 | 9.0 | 8.0 | 8.0 | | | |
| | .260 | 9.0 | | 9.0 | 8.0 | 6.0 | 9.0 | 8.0/9.0 | 6.0 | 3.0 | 9.0 | 9.0 | | 8.0 | | | |
| | .130 | 9.0 | | 9.0 | 8.0 | 9.0 | 9.0 | 7.0 | 4.0 | 1.0 | 9.0 | 9.0 | | 8.0 | | | |
| | .065 | 2.0 | | 9.0 | 3.0 | 7.0 | 9.0 | 8.0 | 7.0 | 9.0 | 9.0 | 9.0 | | 8.0 | | | |
| | .033 | 1.0 | | 8.0 | 2.0 | 7.0 | 9.0 | 6.0 | 8.0 | 6.0 | 6.0 | 6.0 | | 8.0 | | | |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN BR | SUN-FLR XXX | S WHEAT ER |
|---|---|---|---|---|---|---|---|---|---|---|---|---|---|---|---|---|---|
| 7-Ethoxy-2-(5-isopropyl-5-methyl-4-oxo-2-imidazolin-2-yl)-3-quinolinecarboxylic acid | 8.000 | 9.0 | | 9.0 | 9.0 | 9.0 | 9.0 | 8.0 | 9.0 | 9.0 | | 0.0 | 0.0 | 6.0 | 0.0 | 6.0 | |
| | .500 | 0.0 | | 1.0 | 8.0 | 7.0 | 9.0 | 6.0 | 4.0 | 6.0 | | 0.0 | 0.0 | 1.0 | 0.0 | 2.0 | |
| | .250 | 0.0 | | 0.0 | 2.0 | 4.0 | 9.0 | 3.0 | 1.0 | 3.0 | | 0.0 | 0.0 | 1.0 | 0.0 | 2.0 | |
| | .125 | 0.0 | | 0.0 | 2.0 | 0.0 | 2.0 | 0.0 | 1.0 | 0.0 | | 0.0 | 0.0 | 0.0 | 0.0 | 0.0 | |
| | .063 | 0.0 | | 0.0 | 0.0 | 0.0 | | 0.0 | 0.0 | 0.0 | | 0.0 | 0.0 | 0.0 | 0.0 | 0.0 | |
| 6-Chloro-2-(5-isopropyl-5-methyl-4-oxo-2-imidazolin-2-yl)-3-quinolinecarboxylic acid | 4.000 | 9.0 | | 9.0 | 9.0 | 9.0 | | 9.0 | 9.0 | 9.0 | 8.0 | 9.0 | 9.0 | 9.0 | 9.0 | 9.0 | |
| | 1.000 | 9.0 | | 9.0 | 8.0 | 9.0 | | 8.0 | 8.0 | 9.0 | 8.0 | 8.5 | 9.0 | 6.0 | 9.0 | 9.0 | |
| | .500 | 9.0 | | 9.0 | 8.0 | 9.0 | | 9.0 | 9.0 | 9.0 | 7.0 | 9.0 | 9.0 | 5.0 | 9.0 | 9.0 | |
| | .250 | 9.0 | | 9.0 | 8.0 | 8.0 | | 9.0 | 9.0 | 9.0 | 7.0 | 9.0 | 9.0 | 5.0 | 9.0 | 9.0 | |
| | .125 | 9.0 | | | 9.0 | 8.0 | | 9.0 | 7.0 | 9.0 | 5.0 | 9.0 | 9.0 | 3.0 | 9.0 | 8.0 | |
| | .063 | 6.0 | | | 8.0 | 8.0 | | 9.0 | 4.0 | 8.0 | 5.0 | 0.0 | 9.0 | 2.0 | 9.0 | 6.0 | |
| 5-Chloro-2-(5-isopropyl-5-methyl-4-oxo-2-imidazolin-2-yl)-3-quinolinecarboxylic acid | 4.000 | 9.0 | | 9.0 | 8.0 | 9.0 | | 9.0 | 9.0 | 9.0 | 9.0 | 9.0 | 9.0 | 0.0 | 8.0 | 9.0 | |
| | 1.000 | 9.0 | | 9.0 | 9.0* | 9.0 | | 9.0 | 7.0 | 9.0 | 7.0 | 9.0 | 9.0 | | 8.0 | 9.0 | |
| | .500 | 9.0 | | 8.0 | 9.0 | 9.0 | | 9.0 | 9.0 | 9.0 | 5.0 | 9.0 | 9.0 | | 7.0 | 8.0 | |
| | .250 | 9.0 | | 7.0 | 9.0 | 9.0 | 8.0 | 9.0 | 7.0 | 9.0 | 3.0 | 9.0 | 9.0 | | 6.0 | 6.0 | |
| | .125 | 8.0 | | 3.0 | 7.0 | 9.0 | 8.0 | 9.0 | 7.0 | 6.0 | 0.0 | 9.0 | 7.0 | | 3.0 | 6.0 | |
| | .063 | 3.0 | | 0.0 | 2.0 | 7.0 | 6.0 | 9.0 | 2.0 | 0.0 | 0.0 | 9.0 | 5.0 | | 3.0 | 5.0 | |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE, NATO | SOY-BEAN AD | SUN-FLR XXX | S WHEAT ER |
|---|---|---|---|---|---|---|---|---|---|---|---|---|---|---|---|---|---|
| 5-Bromo-2-(5-isopropyl-5-methyl-4-oxo-2-imidazolin-2-yl)-3-quinolinecarboxylic acid | .500 | 8.0 | | 6.0 | 9.0 | 9.0 | 9.0 | 9.0 | 8.0 | 6.0 | | 9.0 | 9.0 | 9.0 | 3.0 | 5.0 | 9.0 |
| | .250 | 4.0 | | 6.0 | 8.0 | 9.0 | 9.0 | 7.0 | 8.0 | 3.0 | | 9.0 | | 7.0 | 2.0 | 4.0 | 7.0 |
| | .125 | 4.0 | | 2.0 | 8.0 | 4.0 | 2.0 | 8.0 | 6.0 | 4.0 | | 9.0 | | 8.0 | 2.0 | 4.0 | 7.0 |
| | .063 | 2.0 | | 1.0 | 8.0 | 4.0 | | 3.0 | | 2.0 | | 9.0 | | 5.0 | 1.0 | 3.0 | 5.0 |
| | .032 | 1.0 | | 1.0 | 8.0 | 1.0 | 2.0 | 2.0 | 4.0 | 0.0 | | 4.0 | | 5.0 | 1.0 | 2.0 | 5.0 |
| | .016 | 0.0 | 0.0 | 0.0 | 5.0 | 1.0 | | 2.0 | 2.0 | 0.0 | | 4.0 | 0.0 | 2.0 | 4.0 | | |
| 4-Chloro-2-(5-isopropyl-5-methyl-4-oxo-2-imidazolin-2-yl)-3-quinolinecarboxylic acid | 4.000 | 2.0 | 0.0 | 9.0 | 1.0 | 9.0 | 2.0 | 9.0 | 0.0 | 9.0 | | 3.0 | | 6.0 | 3.0 | 8.0 | 3.0 |
| | 1000 | 0.0 | 0.0 | 3.0 | 1.0 | 8.0 | 9.0 | 7.0 | 0.0 | 3.0 | | 3.0 | | 3.0 | 3.0 | 2.0 | 1.0 |
| | .500 | 0.0 | 0.0 | 0.0 | 0.0 | 2.0 | 9.0 | 2.0 | 0.0 | 1.0 | | 1.0 | | 2.0 | 0.0 | 0.0 | 0.0 |
| 2-(5-Isopropyl-5-methyl-4-oxo-2-imidazolin-2-yl)-4-methoxy-3-quino- | 8.000 | 8.0 | 9.0 | 9.0 | 7.0 | 9.0 | 9.0 | 9.0 | 9.0 | 9.0 | 6.0 | 9.0 | 3.0 | 4.0 | 4.0 | 9.0 | 4.0 |
| | .500 | 0.0 | | 7.0 | 4.0 | 8.0 | 6.0 | 9.0 | 6.0 | 6.0 | | 6.0 | | 3.0 | 2.0 | 9.0 | 3.0 |
| | .250 | 0.0 | | 4.0 | 3.0 | 7.0 | 6.0 | 3.0 | 5.0 | | | | | 3.0 | 0.0 | 6.0 | |
| | .125 | 0.0 | | 1.0 | 3.0 | 6.0 | | 2.0 | 3.0 | 3.0 | | 3.0 | | 3.0 | 2.0 | 6.0 | 2.0 |

TABLE II-continued

PRE-EMERGENCE TESTS - RATES IN KG/HA

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE NATO | SOY-BEAN WI | SUN-FLR XXX | S WHEAT ER |
|---|---|---|---|---|---|---|---|---|---|---|---|---|---|---|---|---|---|
| linecarboxylic acid | .063 | 0.0 | | 0.0 | 1.0 | 4.0 | 9.0 | 2.0 | | 2.0 | | | | | 1.0 | 3.0 | 1.0 |
| | .032 | 0.0 | | 0.0 | 1.0 | 3.0 | | 2.0 | | 1.0 | | | | | 1.0 | 2.0 | 1.0 |
| 4-Hydroxy-2-(5-isopropyl-5-methyl-4-oxo-2-imidazolin-2-yl)-3-quinoline-carboxylic acid hydrochloride | 8.000 | 9.0 | 7.0 | 6.0 | 5.0 | 9.0 | 9.0 | 9.0 | 9.0 | 8.0 | 2.0 | 2.0 | 2.0 | 1.0 | | | |
| 2-(5-Ethyl-5-methyl-4-oxo-2-imidazolin-2-yl)-3-quinoline-carboxylic acid | .500 | 6.0 | | 9.0 | 7.0 | 7.0 | 9.0 | 7.0 | 4.0 | 6.0 | | 9.0 | | 9.0 | 4.0 | 8.0 | 5.0 |
| | .250 | 3.0 | | 8.0 | 6.0 | 6.0 | 3.0 | 6.0 | 3.0 | 5.0 | | 9.0 | | 8.0 | 3.0 | 5.0 | 3.0 |
| | .125 | 0.0 | | 8.0 | 4.0 | 4.0 | 1.0 | 4.0 | 0.0 | 3.0 | | 9.0 | | 8.0 | 0.0 | 5.0 | 2.0 |
| | .063 | 0.0 | | 2.0 | 4.0 | 2.0 | 0.0 | 2.0 | 0.0 | 1.0 | | 6.0 | | 6.0 | 2.0 | 5.0 | 2.0 |
| 2-(5-Isoproply-5-methyl-4-oxo-2-imidazolin-2-yl)-6,7-dimethyl-3-quinolinecarboxylic acid | .500 | 7.0 | 7.0 | 8.0 | 8.0 | 9.0 | 8.0 | 7.0 | 7.0 | 3.0 | | 9.0 | | 4.0 | 7.0 | 4.0 | 2.0 |
| | .250 | 3.0 | 5.0 | 6.0 | 6.0 | 7.0 | 3.0 | 3.0 | 5.0 | 2.0 | | 8.0 | | 3.0 | 5.0 | | 2.0 |
| | .125 | 1.0 | 2.0 | 4.0 | 4.0 | 7.0 | 3.0 | 3.0 | 5.0 | 6.0 | | 7.0 | | 3.0 | 5.0 | | 2.0 |
| Methyl 2-(5-iso-propyl-5-methyl-4-oxo-2-imidazolin-2-yl)-8-nitro-3-quinolinecarboxylate | 8.000 | 6.0 | 8.0 | 0.0 | 7.0 | 3.0 | 7.0 | 0.0 | 0.0 | 2.0 | | 7.0 | | | 0.0 | | 0.0 |
| 2-(5-Isopropyl-5-methyl-4-oxo-2-imidazolin-2-yl)-4-methyl-3-quinoline-carboxylate | .500 | 2.0 | | 8.0 | 0.0 | 2.0 | 9.0 | 3.0 | 3.0 | 5.0 | | 7.0 | | 9.0 | 0.0 | 6.0 | 0.0 |
| | .250 | 0.0 | | 0.0 | 0.0 | 0.0 | 9.0 | 2.0 | 0.0 | 5.0 | | 5.0 | | 2.0 | 0.0 | 1.0 | 0.0 |
| | .125 | 0.0 | | 0.0 | 0.0* | 0.0 | 3.0 | 1.0 | 0.0 | 4.0 | | 0.0 | | 0.0 | 0.0 | 0.0 | 0.0 |
| | .063 | 0.0 | | 0.0 | 0.0 | 0.0 | 3.0 | 1.0 | 0.0 | 2.0 | | 0.0 | | 0.0 | 0.0 | 0.0 | 0.0 |
| 8-Chloro-2-(5-iso-propyl-5-methyl-4-oxo-2-imidazolin-2-yl)-3-quinoline-carboxylic acid | .500 | 3.0 | | 4.0 | 6.0 | 9.0 | 9.0 | 7.0 | 9.0 | 6.0 | | 9.0 | | 9.0 | 1.0 | 9.0 | 2.0 |
| | .250 | 1.0 | | 3.0 | 4.0 | 7.0 | 9.0 | 5.0 | 9.0 | 5.0 | | 8.0 | | 9.0 | 1.0 | 9.0 | 2.0 |
| | .125 | 1.0 | | 0.0 | 3.0 | 4.0 | 6.0 | 3.0 | 6.0 | 3.0 | | 8.0 | | 7.0 | 1.0 | 7.0 | 1.0 |
| | .063 | 0.0 | | 0.0 | 1.0 | 0.0 | | 2.0 | 0.0 | 1.0 | | 3.0 | | 7.0 | 1.0 | 5.0 | 0.0 |
| | .032 | 0.0 | | 0.0 | 1.0 | 0.0 | 1.0 | 0.0 | 0.0 | 1.0 | | 1.0 | | 4.0 | 0.0 | 5.0 | 0.0 |
| 6-Fluoro-2-(5-iso-propyl-5-methyl-4-oxo-2-imidazolin-2-yl)-3-quinoline-carboxylic acid | .500 | 9.0 | | 9.0 | 9.0 | 9.0 | 9.0 | 9.0 | 9.0 | 9.0 | | 9.0 | | 9.0 | 4.0 | 9.0 | 9.0 |
| | .250 | 9.0 | | 8.0 | 9.0 | 9.0 | 9.0 | 9.0 | 8.0 | 8.0 | | 9.0 | | 9.0 | 4.0 | 9.0 | 8.0 |
| | .125 | 3.0 | | 9.0 | 9.0 | 9.0 | 9.0 | 7.0 | 8.0 | 7.0 | | 8.0 | | 9.0 | 2.0 | 8.0 | 8.0 |
| | .063 | 2.0 | | 9.0 | 9.0 | 8.0 | 7.0 | 6.0 | 2.0 | 6.0 | | 2.0 | | 6.0 | 1.0 | 7.0 | 5.0 |
| | .032 | 1.0 | | 7.0 | 9.0 | 3.0 | 7.0 | 7.0 | 7.0 | 7.0 | | 9.0 | | 9.0 | 6.0 | 9.0 | 8.0 |
| 2-(5-Isopropyl-5-methyl-4-oxo-2-imidazolin-2-yl)-3-quinoline-carboxylic acid | .500 | 7.0 | | 9.0 | 9.0 | 9.0 | 6.0 | 6.0 | 1.0 | 2.0 | | 9.0 | | 8.0 | 4.0 | 9.0 | 7.0 |
| | .250 | 7.0 | | 8.0 | 9.0 | 9.0 | 4.0 | 6.0 | 0.0 | 2.0 | | 9.0 | | 8.0 | 2.0 | 9.0 | 7.0 |
| | .125 | 3.0 | | 7.0 | 3.0 | 9.0 | 6.0 | 1.0 | 0.0 | 0.0 | | 9.0 | | 8.0 | 1.0 | 8.0 | 3.0 |
| 8-methoxy-3-quino-linecarboxylic acid | .063 | 2.0 | | 7.0 | 0.0 | 9.0 | 4.0 | 0.0 | 0.0 | 0.0 | | 9.0 | | 7.0 | | 7.0 | 1.0 |
| | .032 | 0.0 | | 2.0 | 0.0 | 9.0 | | | | | | | | | | | |

| Compound | RATE | BARN-YARD GR | GREEN FOX | P NUT-SEDGE | WILD OATS | QUACK-GRASS | FLD BIND-WD | MRN-GLRY SP | RAG-WEED | VELVET-LEAF | S BARLY LA | CORN FIELD | COT-TON | RICE NATO | SOY-BEAN WI | SUN-FLR XXX | S WHEAT ER |
|---|---|---|---|---|---|---|---|---|---|---|---|---|---|---|---|---|---|
| 2-(5-Isopropyl-5-methyl-4-oxo-2-imidazolin-2-yl)- | .500 | 7.0 | | 0.0 | 9.0 | 9.0 | 9.0 | 8.0 | 9.0 | 5.0 | | 8.0 | | 9.0 | 9.0 | 8.0 | |
| | .250 | 5.0 | | 0.0 | 8.0 | 4.0 | 9.0 | 1.0 | 8.0 | 2.0 | | 2.0 | | 7.0 | 9.0 | 7.0 | |
| | .125 | 1.0 | | 0.0 | 8.0 | 1.0 | 0.0 | | 4.0 | 2.0 | | 2.0 | | 5.0 | 8.0 | 5.0 | |
| 6-(trifluoro-methyl)-3-quino-linecarboxylic acid | .063 | 0.0 | | 0.0 | 3.0 | 0.0 | 0.0 | 0.0 | 0.0 | 0.0 | | 1.0 | | 2.0 | 7.0 | 2.0 | |

What is claimed is:

1. A compound having the structure:

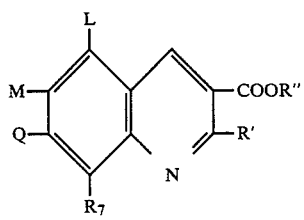

wherein R' is $CH_3$ or COOR"; R" is $C_1$–$C_4$ alkyl; L, M, Q and $R_7$ are each H, Cl, Br, F, I, $C_1$–$C_4$ alkyl, $C_1$–$C_4$ alkoxy, $C_1$–$C_4$ alkylthio, $C_1$–$C_4$ alkylsulfonyl, halo($C_1$–$C_4$)alkyl, $NO_2$, CN, phenyl, phenoxy, difluoromethoxy, loweralkylamino, chlorophenyl or phenoxy substituted with one Cl, $CF_3$, $NO_2$ or $CH_3$ group, with the proviso that at least one of L, M, Q and $R_7$ is a substituent other than hydrogen and that only one of L, M, Q or $R_7$, may represent a substituent other than hydrogen, halogen, $C_1$–$C_4$ alkyl or $C_1$–$C_4$ alkoxy, with the further proviso that at least two of L, M, Q and $R_7$ are hydrogen.

2. A compound according to claim 1 wherein R' is $CH_3$, $COOCH_3$ or $COOC_2H_5$; R" is $CH_3$ or $C_2H_5$; L, M, Q and $R_7$ are each H, Cl, Br, $C_1$–$C_4$ alkyl, $C_1$–$C_2$ alkoxy, $CF_3$, $NO_2$, CN, phenyl, phenoxy or difluoromethoxy; with the proviso that at least one of L, M, Q and $R_7$ is a substituent other than H and that only one of L, M, Q or $R_7$ may represent a substituent other than hydrogen, $C_1$–$C_4$ alkyl or $C_1$–$C_2$ alkoxy.

3. A compound according to claim 1 wherein L, M, and Q are hydrogen; $R_7$ is methoxy; R' is $COOCH_3$ and R" is $CH_3$.

4. A compound according to claim 1 wherein L, Q and $R_7$ are hydrogen; M is Cl; R' is $COOCH_3$ and R" is $CH_3$.

5. A compound according to claim 1 wherein L, Q and $R_7$ are hydrogen; M is $OCHF_2$; R' is $COOCH_3$ and R" is $CH_3$.

6. A compound according to claim 1 wherein L, Q and $R_7$ are hydrogen; M is $NO_2$; R' is $COOCH_3$ and R" is $CH_3$.

* * * * *